(12) United States Patent
Li et al.

(10) Patent No.: US 9,260,461 B2
(45) Date of Patent: Feb. 16, 2016

(54) WATER-SOLUBLE DERIVATIVES AND PRODRUGS OF ACACETIN AND METHODS OF MAKING AND USING THEREOF

(71) Applicants: Versitech Limited, Hong Kong (CN); Shanghai Institute of Pharmaceutical Industry, Shanghai (CN)

(72) Inventors: Gui-Rong Li, Hong Kong (CN); Feng Lin, Shanghai (CN)

(73) Assignee: Versitech Limited, Hong Kong (HK)

( * ) Notice: Subject to any disclaimer, the term of this patent is extended or adjusted under 35 U.S.C. 154(b) by 0 days.

(21) Appl. No.: 14/171,228

(22) Filed: Feb. 3, 2014

(65) Prior Publication Data

US 2015/0218193 A1  Aug. 6, 2015

(51) Int. Cl.
  *A61K 31/35* (2006.01)
  *C07D 311/00* (2006.01)
  *C07F 9/655* (2006.01)

(52) U.S. Cl.
  CPC .................................. *C07F 9/65522* (2013.01)

(58) Field of Classification Search
  CPC .......................... A61K 31/352; A61K 31/7016
  USPC ............................................ 514/456; 549/402
  See application file for complete search history.

(56) References Cited

U.S. PATENT DOCUMENTS 7,816,400 B2 * 10/2010 Li et al. .......................... 514/456
8,461,198 B2 *  6/2013 Li et al. .......................... 514/456

FOREIGN PATENT DOCUMENTS

| CN | 102697769 | 10/2012 | | |
|---|---|---|---|---|
| CN | 103058975 | 10/2012 | | |
| WO | WO 2014134419 A1 * | 9/2014 | ............. | A61K 31/00 |

* cited by examiner

Primary Examiner — My-Chau T Tran
(74) Attorney, Agent, or Firm — Pabst Patent Group LLP

(57) ABSTRACT

Water-soluble derivatives and/or prodrugs of acacetin are described herein. The compounds can be used as cardioprotection agents against myocardial infarction induced by ischemia-reperfusion. In one embodiment the compounds are used to treat ischemic cardiac diseases. In the preferred embodiment, the compounds are used to treat and/or prevent myocardial infarction in humans.

20 Claims, 17 Drawing Sheets

Heart slices [TTC stain] in vivo rats with
30 min ischemia followed by 2 h reperfusion

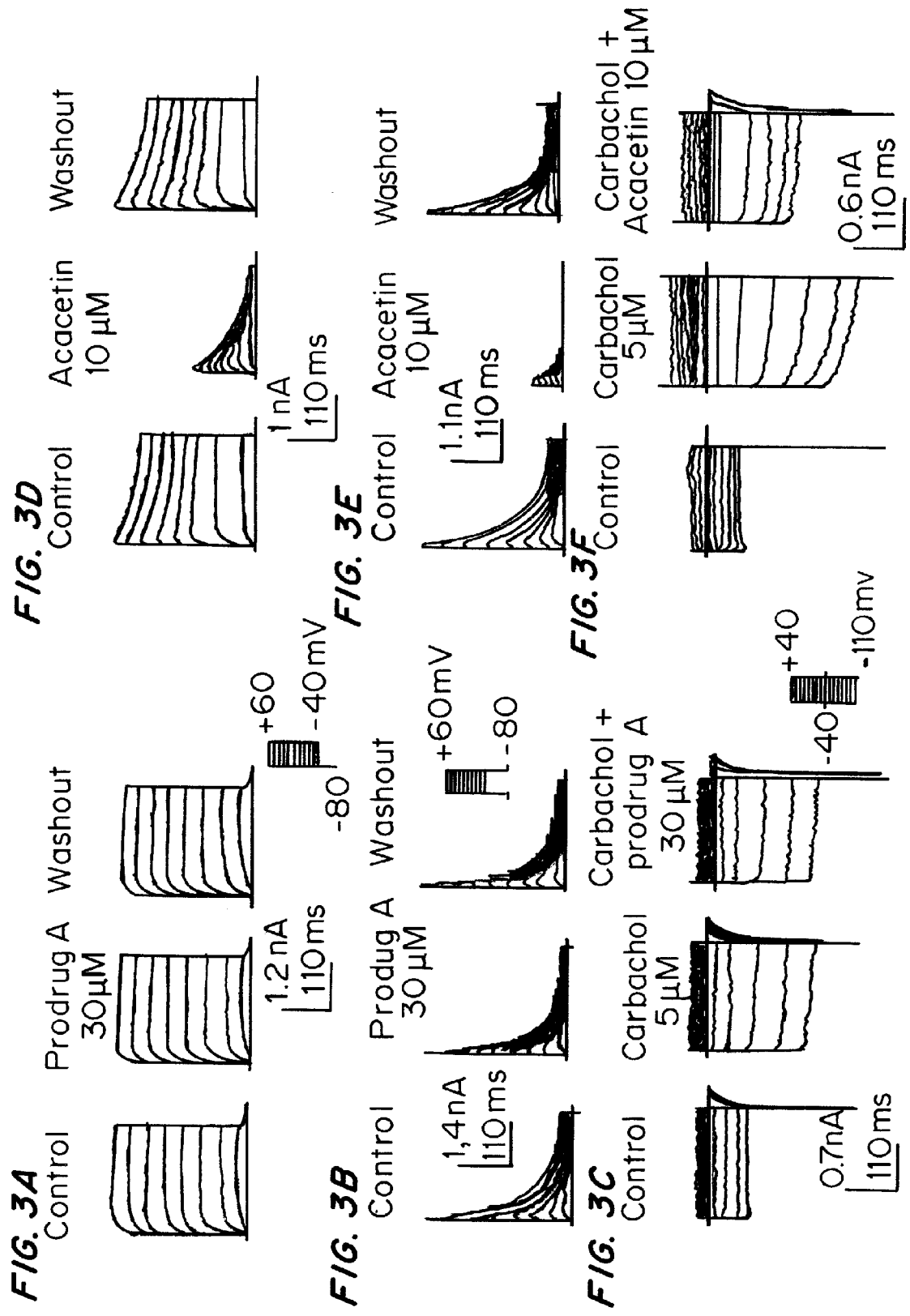

HPLC_Blank blood sample before Prodrug A in a rat

HPLC_blood sample after Prodrug A (20mg/kg i.v., 10 min) in a rat

Time-dependent concentrations of acacetin in blood plasma with i.v. infusion of prodrugs in rats

| Time (min) | 0 | 2 | 10 | 15 | 30 | 45 | 60 | 90 |
|---|---|---|---|---|---|---|---|---|
| Prodrug A Acacetin, ng/mL | 0 | 965.5 ±94.6 | 1837.1 ±12.2 | 2111 ±379 | 1688.9 ±383.7 | 234.1 ±88 | 191.7 ±79.9 | 137.5 ±1 |
| Prodrug B (Acacetin, ng/mL) | 0 | 873.1 ±54.7 | 1076.9 ±12 | 1384 ±51 | 1696.8 ±8.7 | 1737.1 ±88 | 1218.5 ±24.6 | 144.1 ±1 |
| Prodrug C (Acacetin, ng/mL) | 0 | 298.9 ±94.6 | 984.1 ±269.4 | 1157.1 ±241.8 | 1144.6 ±356.6 | 228.6 ±38.9 | 74.7 ±16.5 | 35.2 ±1.1 |

Note: Prodrug A&C (20 mg/kg for 30 min i.v. infusion, n=3-4)
Prodrug B (20 mg/kg for 60 min i.v. infusion, n=3)

FIG. 4C

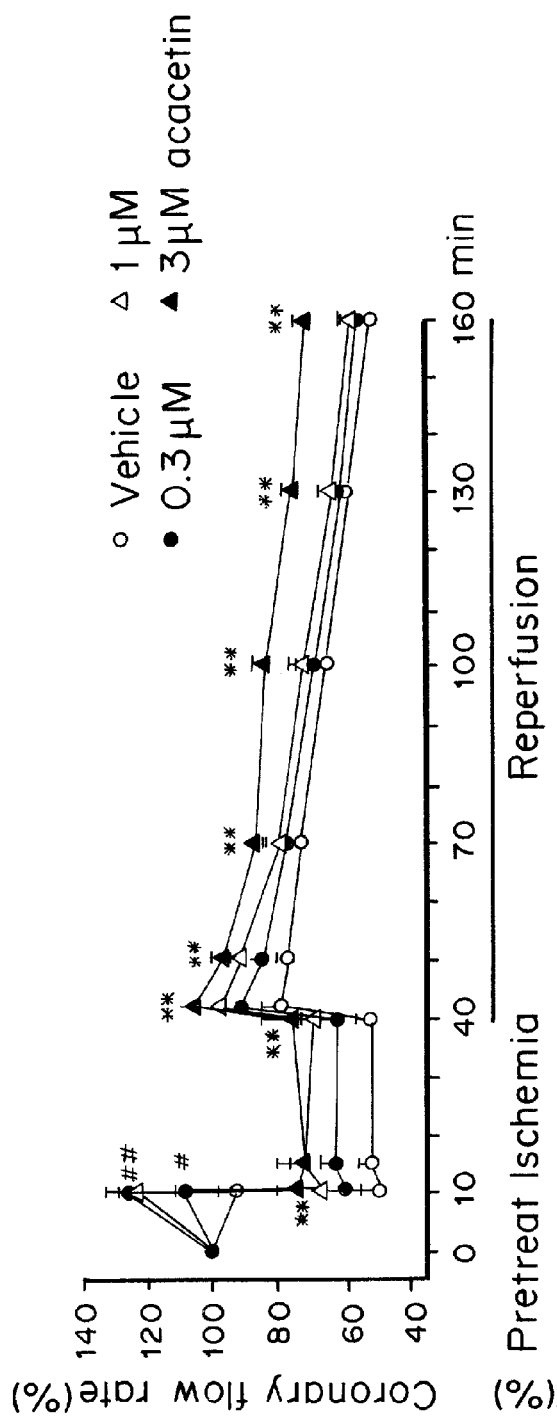
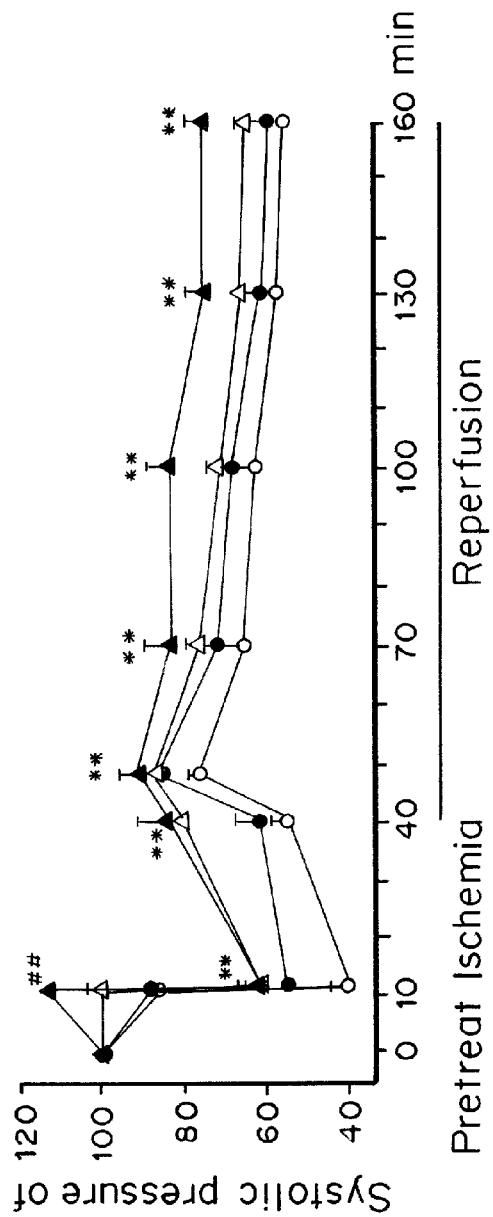
FIG. 5A
FIG. 5B

Vehicle

Acacetin 3μM

WATER-SOLUBLE DERIVATIVES AND PRODRUGS OF ACACETIN AND METHODS OF MAKING AND USING THEREOF

FIELD OF THE INVENTION

This invention is in the field of water-soluble derivatives and/or prodrugs of acacetin and methods of making and using thereof.

BACKGROUND OF THE INVENTION

Myocardial infarction is a major risk for cardiac death in patients suffering from myocardial ischemia followed by reperfusion injury. During cardiac ischemia, the balance of metabolic supply and demand is broken and myocardial tissue undergoes hypoxia stress, the blood reflow (reperfusion) of the ischemic myocardium induces re-oxygenation, which results in further tissue injury and a series of intracellular responses. These responses trigger life threatening ventricular fibrillation and are accompanied by acute inflammatory responses, metabolic disorder, apoptosis, and necrosis. These may also result from cardiac dysfunction and remodelling.

Studies on anti-ischemia-reperfusion injury have long focused on preconditioning and post-conditioning cardioprotection against myocardial injury caused ischemia-reperfusion. Such studies have provided insight into the intracellular molecular signals involved in the ischemia-reperfusion injury (e.g. ROS, TNFα, polymorphonuclear leukocytes infiltration, apoptosis signals, etc.) and preconditioning and postconditioning cardioprotection (e.g. adenosine, bradykinin, and opioid peptides, SOD, etc.).

These ischemia-reperfusion-related molecular signals are potential pharmacological targets. A number of pharmacological agents including β-adrenoreceptor blockers, adenosine, cyclosporine, and nitric oxide have been studied clinical patients. However, there are no approved drugs to prevent the sudden death caused by acute myocardial infarction (heart attack).

Acacetin, obtained from the Chinese medicinal herb Tianshanxuelian, inhibits atrial IKur, IKACh, and Ito and prevents the induction of experimental atrial fibrillation in anesthetized canines after duodenal administration. Chinese Patent Application 102697769A describes the use of acacetin in an anti-ischemia/reperfusion-injury model. Chinese Patent Application No. 103058975A describes the use of acacetin in an ex vivo brain model for stroke. Clinically, an intravenous preparation is required to rescue acute atrial fibrillation or myocardial infarction. However, acacetin is water-insoluble and therefore cannot be administered intravenously in a straight forward manner.

There exists a need for water-soluble derivatives and/or water-soluble prodrugs of acacetin that can be rapidly administered intravenously to prevent sudden death from myocardial infarction.

Therefore, it is an object of the invention to provide water-soluble derivatives and/or water-soluble prodrugs of acacetin that can be rapidly administered intravenously to prevent sudden death from myocardial infarction, and methods of making and using thereof.

SUMMARY OF THE INVENTION

Water-soluble derivatives and/or prodrugs of acacetin are described herein. The compounds can be used as cardioprotection agents against myocardial infarction induced by ischemia-reperfusion. In one embodiment the compounds are used to treat ischemic cardiac diseases. In the preferred embodiment, the compounds are used to treat and/or prevent myocardial infarction in humans.

In one embodiment, the water-soluble derivative or compound is a compound of Formula I:

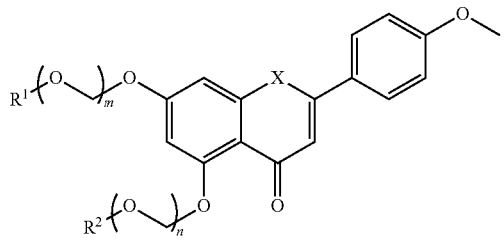

wherein m and n are independently an integer from 0 to 3;

X is O or N or S;

$R^1$ and $R^2$ are independently hydrogen, alkyl, alkenyl, alkynyl, cycloalkyl, cycloalkenyl, cycloalkynyl, heterocyclyl, aryl, alkaryl, arylalkyl, carboxyalkyl, amino, aminoalkyl, alkylamino, dialkylamino, arylamino, diarylamino, alkylarylamino, hydroxyalkyl, alkoxyalkyl, acyl, $PO_3H_2$, $PO_3^{2-}M$, where M is one or more ammonium ions, alkali metal ions, or alkaline earth metal ions, phosphate ester, $SO_3H$, $SO_3^-M$, where M is an ammonium ion, alkali metal ion, or alkaline earth metal ion, sulfonic ester, sulfonamide, —C(=O)-$A^1$ or —C(=O)-L-$A^2$;

wherein $A^1$ and $A^2$ are independently hydrogen, halo, alkoxy, hydroxy, thiol, alkyl, alkenyl, alkynyl, cycloalkyl, cycloalkenyl, cycloalkynyl, alkaryl, arylalkyl, carbamate, amino, alkylamino, arylamino, dialkylamino, alkylarylamino, diarylamino, sulfonamide, heteroalkyl; and L is alkylene, alkenylene, alkynylene, arylene, aralkylene or alkarylene, or a pharmaceutically acceptable salt thereof.

In some embodiments, the compound is a compound of Formula IIA:

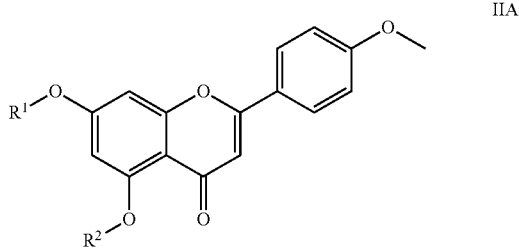

wherein

X=O; m=0; n=0;

$R^1$ are $R^2$ are independently hydrogen, $PO_3H_2$, $PO_3^{2-}M$, wherein M is one or more ammonium ions, alkali metal ions, or alkaline earth metal ions, $SO_3H$, $SO_3^-M$, wherein M is an ammonium ion, alkali metal ion, or alkaline earth metal ion, phosphate ester, sulfonic ester or sulfonamide;

wherein, when $R^2$ is H, $R^1$ is not H or sulfonate;

or a pharmaceutically acceptable salt thereof.

In still other embodiments, the compound is a compound of Formula IIB:

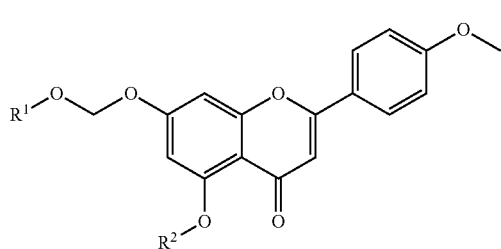

wherein:

X=O; m=1; n=0;

R¹ are R² are independently hydrogen, $PO_3H_2$, $PO_3^{2-}M$, wherein M is one or more ammonium ions, alkali metal ions, or alkaline earth metal ions, phosphate ester, $SO_3H$, $SO_3^-M$, wherein M is an ammonium ion, alkali metal ion, or alkaline earth metal ion, sulfonic ester or sulfonamide;

wherein when R² is H, R¹ is not H; or a pharmaceutically acceptable salt thereof.

BRIEF DESCRIPTION OF THE DRAWINGS

FIG. 3A is a graph showing the effect of Prodrug A on Kv1.5 current expressed in HEK 293 cells. FIG. 3B is a graph showing the effect of Prodrug A on Kv4.3 current expressed in HEK 293 cells. FIG. 3C is a graph showing the effect of Prodrug A on IKACh activated by 5 μM carbachol in rat atrial myocytes. FIG. 3D is a graph showing the effect of acacetin on Kv1.5 current in HEK 293 cells. FIG. 3E is a graph showing the effect of acacetin on Kv4.3 current in HEK 293 cells. FIG. 3F is a graph showing the effect of acacetin on IKACh activated by 5 μM carbachol in rat atrial myocytes.

FIG. 4C is a table showing the concentrations of acacetin in blood samples over time after administration of Prodrugs A, B, and C.

FIG. 5A is a graph showing the effect of acacetin concentration on the coronary flow rate (%) as a function of time. FIG. 5B is a graph showing the effect of acacetin concentration on the systolic pressure of LV (%) as a function of time.

DETAILED DESCRIPTION OF THE INVENTION

I. Definitions

Figure 1A:
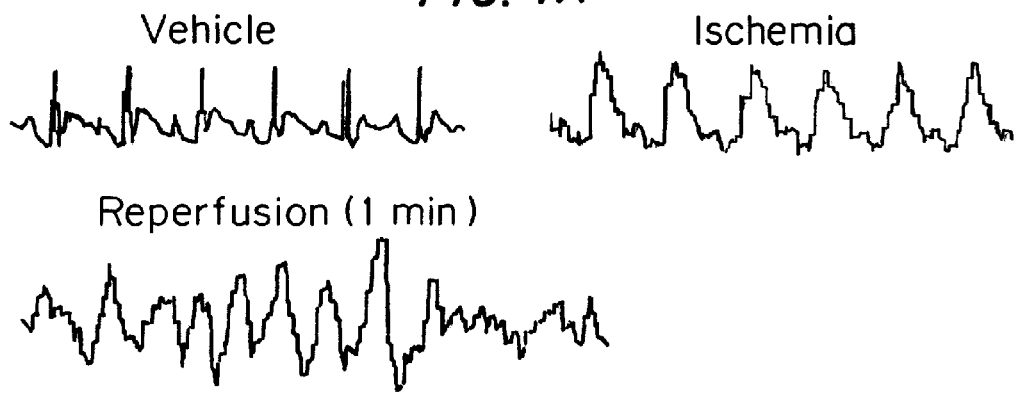
FIG. 1A is an ECG in a rat treated with vehicle (equivolume Tris, pH=7.2), showing the ventricular fibrillation after reperfusion for 1 min.

In describing and claiming the disclosed subject matter, the following terminology will be used in accordance with the definitions set forth below.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The alkyl groups can also be substituted with one or more groups including, but not limited to, halogen, hydroxy, amino, thio, ether, ester, carboxy, oxo, and aldehyde groups. The alkyl groups may also contain one or more heteroatoms. "Lower alkyl", as used herein, means 1-6 carbons, preferably 1-5 carbons, more preferably 1-4 carbons, most preferably 1-3 carbons.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O— alkynyl. Aroxy can be represented by —O-aryl or O-heteroaryl, wherein aryl and heteroaryl are as defined below. The alkoxy and phenoxyl groups can be substituted as described above for alkyl.

"Phosphate ester" as used herein refers is represented by the general formula:

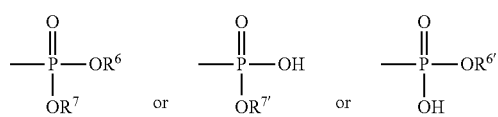

wherein, $R^6$, $R^7$, $R^{6'}$ and $R^{7'}$ each independently represent an alkyl, a cycloalkyl, an alkenyl, an cycloalkenyl, an alkynyl, an aryl, an alkaryl or an arylalkyl. In some embodiments, $R^6$ and $R^7$ (and optionally $R^{6'}$ or $R^{7'}$) each independently represent an aryl.

The terms "amine" and "amino" are art-recognized and refer to both unsubstituted and substituted amines, e.g., a moiety that can be represented by the general formula:

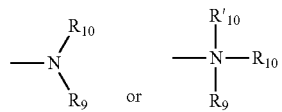

wherein, $R_9$, $R_{10}$, and $R'_{10}$ each independently represent hydrogen, alkyl, alkenyl, alkynyl, cycloalkyl, cycloalkenyl, aryl, heteroaryl, alkylaryl, arylalkyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a heteroaryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R_{10}'$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula:

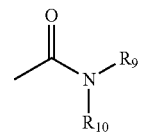

wherein $R_9$ and $R_{10}$ are as defined above.

"Aryl" as used herein, refers to 5-, 6- and 7-membered aromatic, heterocyclic, fused aromatic, fused heterocyclic, biaromatic (e.g., biphenyl), or bihetereocyclic (e.g., bipyridinyl) ring system, optionally substituted with one or more substituents including, but not limited to, by halogen, hydroxy, nitro, cyano, amino, primary, secondary, or tertiary amino, formyl, acyl, carboxylate, alkoxy, thioether, alkyl, alkenyl, and alkynyl, cycloalkyl, etc. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Aryl" includes substituted and unsubstituted biaryl and biheteroaryl compounds, optionally interrupted or bridged by one more atoms such as carbon and/or heteroatoms (e.g., O, S, N, etc.). Examples include, but are not limited to, biaryl ethers, biaryl amines, biaryl thiols, biheteroaryl ethers, biheteroaryl amines and biheteroaryl thiols.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $(C_{1-4})$ alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, $(C_1-C_8)$ alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like. The ring can be unsubstituted or substituted.

"Halogen", as used herein, refers to fluorine, chlorine, bromine, or iodine.

The term "carbonyl" is art-recognized and includes such moieties as can be represented by the general formula:

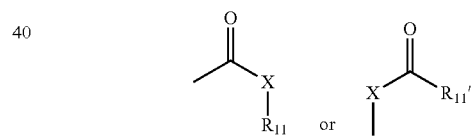

wherein, X is a bond or represents an oxygen or a sulfur, and $R_{11}$ represents a hydrogen, an alkyl, a cycloalkyl, a heterocycloalkyl, an alkenyl, an cycloalkenyl, a heterocycloalkenyl, an alkynyl, an aryl, or a heteroaryl, $R'_{11}$ represents a hydrogen, an alkyl, a cycloalkyl, a heterocycloalkyl, an alkenyl, an cycloalkenyl, a heterocycloalkenyl, an alkynyl, an aryl, or a heteroaryl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is a hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen; the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium. Other heteroatoms include silicon and arsenic.

As used herein, the term "nitro" means $-NO_2$; the term "halogen" designates —F, —Cl, —Br or —I; the term "sulfhydryl" means —SH; the term "hydroxyl" means —OH; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) which is administered in an inactive (or significantly less active) form. Once administered, the prodrug is metabolized in the body (in vivo) into the active compound.

The term "therapeutically effective" or "effective amount" means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

The term "patient" or "subject" to be treated refers to either a human or non-human animal.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diastereomers can be resolved or separated using techniques known in the art. "Chirality" also includes axial and planar chirality.

II. Compounds

Water-soluble derivatives and/or prodrugs of acacetin are described herein. The compounds can be used as cardioprotection agents against myocardial infarction induced by ischemia-reperfusion. In one embodiment the compounds are used to treat ischemic cardiac diseases. In the preferred embodiment, the compounds are used to treat and/or prevent myocardial infarction in humans.

In one embodiment, the water-soluble derivative or compound is a compound of Formula I:

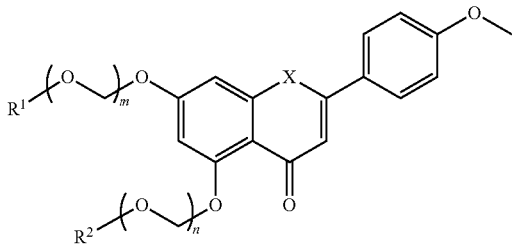

wherein
m and n are independently an integer from 0 to 3;
X is O or N or S;
$R^1$ and $R^2$ are independently hydrogen, alkyl, alkenyl, alkynyl, cycloalkyl, cycloalkenyl, cycloalkynyl, heterocyclyl, aryl, alkaryl, arylalkyl, carboxyalkyl, amino, aminoalkyl, alkylamino, dialkylamino, arylamino, diarylamino, alkylarylamino, hydroxyalkyl, alkoxyalkyl, acyl, $PO_3H_2$, $PO_3^{2-}M$, where M is one or more ammonium ions, alkali metal ions, or alkaline earth metal ions, phosphate ester, $SO_3H$, $SO_3^-M$, where M is an ammonium ion, alkali metal ion, or alkaline earth metal ion, sulfonic ester, sulfonamide, $—C(=O)-A^1$ or $—C(=O)-L-A^2$;
wherein $A^1$ and $A^2$ are independently hydrogen, halo, alkoxy, hydroxy, thiol, alkyl, alkenyl, alkynyl, cycloalkyl, cycloalkenyl, cycloalkynyl, alkaryl, arylalkyl, carbamate, amino, alkylamino, arylamino, dialkylamino, alkylarylamino, diarylamino, sulfonamide, heteroalkyl; and
L is alkylene, alkenylene, alkynylene, arylene, aralkylene or alkarylene,
or a pharmaceutically acceptable salt thereof.

In some embodiments, the compound is a compound of Formula IIA:

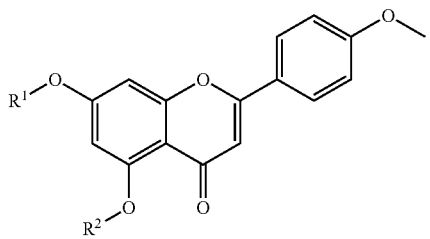

wherein
X=O; m=0; n=0;
$R^1$ are $R^2$ are independently hydrogen, $PO_3H_2$, $PO_3^{2-}M$, wherein M is one or more ammonium ions, alkali metal ions, or alkaline earth metal ions, $SO_3H$, $SO_3^-M$, where M is an ammonium ion, alkali metal ion, or alkaline earth metal ion, phosphate ester, sulfonic ester or sulfonamide;
wherein, when $R^2$ is H, $R^1$ is not H or sulfonate;
or a pharmaceutically acceptable salt thereof.

In still other embodiments, the compound is a compound of Formula IIB:

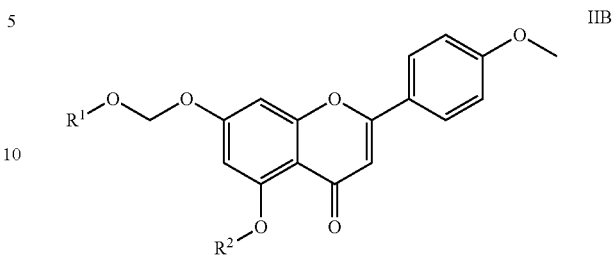

wherein:
X=O; m 1; n=0;
$R^1$ are $R^2$ are independently hydrogen, $PO_3H_2$, $PO_3^{2-}M$, wherein M is one or more ammonium ions, alkali metal ions, or alkaline earth metal ions, phosphate ester, $SO_3H$, $SO_3^-M$, wherein M is an ammonium ion, alkali metal ion, or alkaline earth metal ion, sulfonic ester or sulfonamide;
wherein when $R^2$ is H, $R^1$ is not H; or a pharmaceutically acceptable salt thereof.

In particular embodiments, the compound is Prodrug A, B, or C:

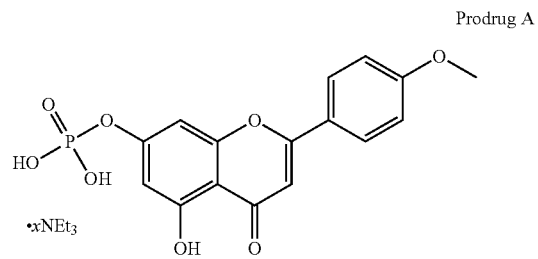

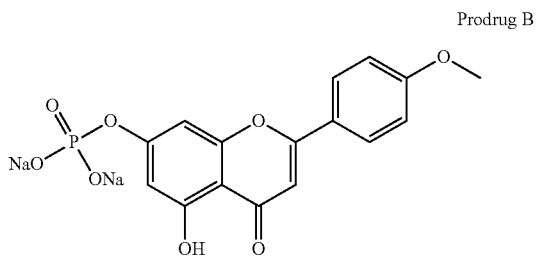

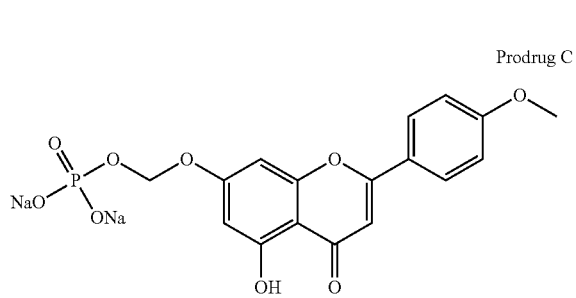

Other compounds are shown below:

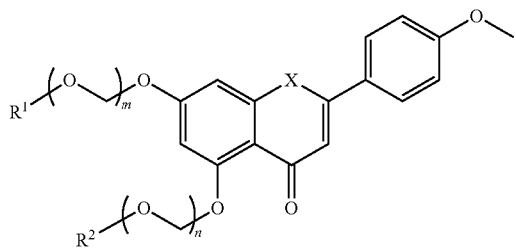

| Compound | X | m | n | R¹ | R² |
|---|---|---|---|---|---|
| A-1 | O | 0 | 0 | P(O)(OCH$_2$C$_6$H$_5$)$_2$ | H |
| Prodrug A | O | 0 | 0 | P(O)(OH)$_2$·x(NEt$_3$) | H |
| B-1 | O | 0 | 0 | P(O)(OBn)$_2$ | H |
| B-2 | O | 0 | 0 | P(O)(OH)$_2$ | H |
| Prodrug B | O | 0 | 0 | P(O)(ONa)$_2$ | H |
| C-2 | O | 1 | 0 | P(O)(OH)$_2$ | H |
| Prodrug C | O | 1 | 0 | P(O)(ONa)$_2$ | H |

Prodrug A: C$_{16}$H$_{13}$O$_8$P·x(C$_6$H$_9$N)

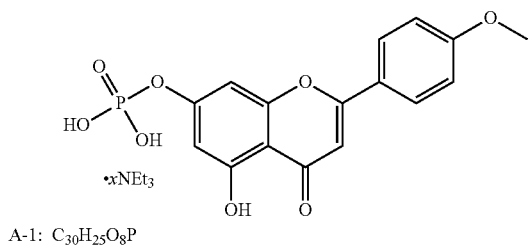

A-1: C$_{30}$H$_{25}$O$_8$P

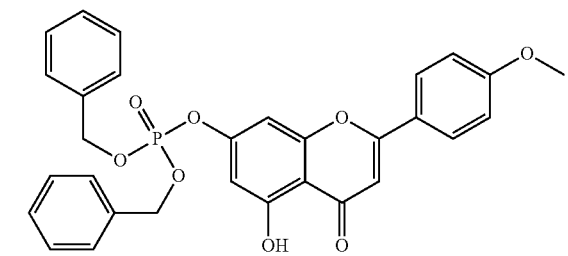

Prodrug B: C$_{16}$H$_{11}$O$_8$PNa$_2$

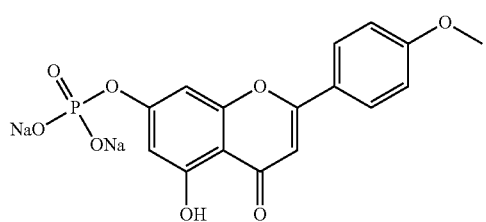

B-1: C$_{30}$H$_{25}$O$_8$P

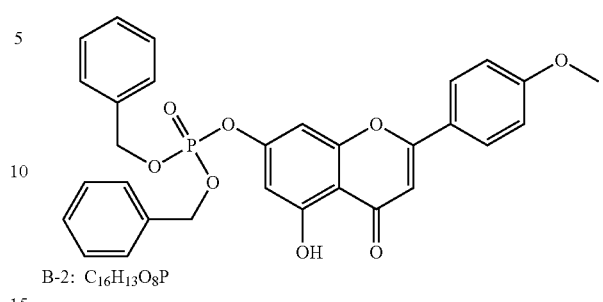

B-2: C$_{16}$H$_{13}$O$_8$P

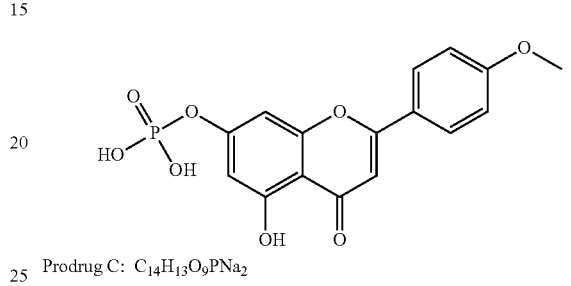

Prodrug C: C$_{14}$H$_{13}$O$_9$PNa$_2$

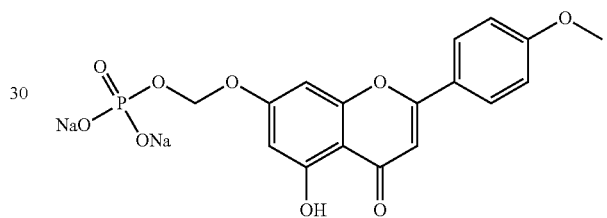

C-2: C$_{17}$H$_{15}$O$_9$P

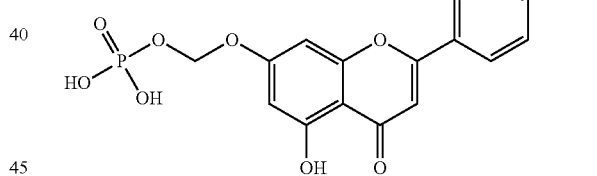

III. Pharmaceutical Compositions

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

i. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten. Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Injectable/Implantable Solid Implants

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent. Alternatively, the compounds can be incorporated into a polymer matrix and molded, compressed, or extruded into a device that is a solid at room temperature. For example, the compounds can be incorporated into a biodegradable polymer, such as polyanhydrides, polyhydroxyalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art.

A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit) L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

1. Topical Formulations

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water, tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more compounds to a patient in need thereof. For topical applications, repeated application can be done or a patch can be used to provide continuous administration of the compounds over an extended period of time.

D. Pulmonary Formulations

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm3, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

E. Other Agents

The formulations containing the water-soluble derivative and/or prodrug can further contain one or more additional active agents. Suitable agents include, but are not limited to, the parent compound acacetin; other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron); calcium channel blockers; cyclooxygenase inhibitors (i.e., COX-1 and/or COX-2 inhibitors) such as aspirin, indomethacin, ibuprofen, piroxicam, Naproxen@, Celebrex®, Vioxx® and NSAIDs; anti-platelet agents; diuretics; and combinations thereof.

IV. Methods of Use

The water-soluble derivatives and/or prodrugs of acacetin described herein can be used to treat a variety of disorders. Exemplary disorders include, but are not limited to, cardiac disorders, such as atrial fibrillation, myocardial infarction, cardiomyopathy, etc.; vascular disorders, such as arthrosclerosis, stroke, etc.; neurological disorders, such as Alzheimer's disease and associated disorders; liver disorders, such as hepatitis and cirrhosis; kidney damage, such as from drugs and/or toxins; immune disorders, such as lupus and other autoimmune diseases; metabolic disorders, such as diabetes, hyperlipidemia, hypercholesterolemia, etc. and cancers, such as breast cancer, prostate cancer, leukemia, etc.

In one embodiment, the compounds described herein are used as cardioprotection agents, for example, in the treatment of myocardial infarction induced by ischemia-reperfusion injury. The compounds described herein have been shown to reduce the myocardial infarct size and inhibit the ventricular fibrillation caused by ischemia-reperfusion injury. The mechanism is believed to involve the suppression of apoptosis, autophagy, oxidation, and inflammation induced by ischemia-reperfusion injury. The compounds described herein can be used for the treatment of diseases in mammals, including humans, and especially for the management of human myocardial infarction. The compounds can also be used to treat or prevent ventricular fibrillation resulting from coronary spasm and/or myocardial reperfusion during/after coronary stent grafting in patients who are suffered from coronary artery blockage.

Intravenous administration of the compounds described herein, such as prodrug A (e.g., 10 mg/kg) antagonizes myocardial infarction induced by ischemia-reperfusion (10 min coronary ligation followed by 10 min reperfusion) in anesthetized rats, decreases the ventricular arrhythmia score, reduces the duration of arrhythmias, and inhibits ventricular fibrillation in a dose-dependent manner (e.g., 5 mg/kg, 10 mg/kg, and 20 mg/kg).

It has been found that intravenous administration of the water-soluble compounds described herein, such as prodrug A, in rats significantly prevents the heart rate reduction and improves the reduced ventricular contractile function induced by ischemia-reperfusion injury, including left ventricular systolic pressure, left ventricular pressure development, and +dP/dT of left ventricular systolic pressure in a dose-dependent manner. It has been found that the compounds described herein, such as prodrug A (e.g., 10 mg/kg, i.v.), reduces the ventricular infarct area indicating that the cardioprotection is related to anti-myocardial infarction.

The compositions contain an effective amount of one or more water-soluble derivatives and/or prodrugs to provide cardioprotection. The amount of agent or agents to be administered can be readily determined by the prescribing physician and is dependent on a variety of conditions, including age and weight of the patient, disorder or disorders to be treated, and other underlying diseases or disorders. In some embodiments, the amount of drug to be administered is from about 0.001 to about 100 mg/kg of the body weight of the patient per day.

Kits containing the one or more agents and directions for their use are also described herein. The kit can include one or more containers containing the one or more agents, one or more devices to administer the agents, such a syringe, and instructions for preparing and administering the agents. In some embodiments, the kit may contain one or more solvents to prepare a solution or suspension of the agent.

EXAMPLES

Materials and Methods

Whole Animal Experiments

The animal study follows the Guide for the Care and Use of Laboratory Animals published by the US National Institutes of Health (NIH Publication No. 85-23, revised 1996), and the experimental procedure was approved by the Committee on the Use of Live Animals in Teaching and Research of the University of Hong Kong.

Ischemia-Reperfusion Model in Anesthetized Rats

Adult male Sprague-Dawley (SD) rats (250-300 g) were anesthetized with pentobarbital (30 mg/kg i.p.), supplemented during the experiment when needed. The animal was intubated and ventilated. Body temperature was maintained at 37° C. with a temperature control system. The jugular vein was cannulated for drug administration and a plastic tubing (0.8 mm OD) was introduced into the left ventricle through the jugular artery to measure the contractile function (e.g. left ventricular pressure). The left chest was opened under ventilation to expose the coronary artery. A fine silk was introduced at the upper ⅓ left anterior coronary descending artery (LA). After a 10-min stabilization period, the drug at 5, 10, or 20 mg/kg was intravenously administrated respectively in 5 min, and an equal volume (1 mL/kg) of vehicle was administrated for the control. LAD was then ligated for 10 min followed a 30-min reperfusion. ECG and blood pressure signals were continuously monitored and stored on an IBM compatible PC computer using a multiple channels data acquisition system (RM-6280C, Chengdu Instrument Ltd, Chendu, China) to record the incidence of ventricular arrhythmia (i.e. fibrillation, tachycardia, and premature beats) and change in was recorded.

Blood Sample Collection in Anesthetized Rats for HPLC Analysis

Male SD rats (250-300 g) was anesthetized with phenobarbital (30 mg/kg, i.p.), and the jugular vein and femoral vein were cannulated for drug administration and blood sample collection. Tracheal cannulation was also performed for ventilation. Drug (20 mg/kg) was administered for 30-60 min, and blood samples (~0.2 mL) were collected before and at 5, 15, 30, 60, 90, and 120 min after drug administration using ascorbic acid and EDTA-preserved microcentrifuge tubes (1.5 mL) for HPLC (high-performance liquid chromatography) analysis of acacetin conversion.

The samples were stored in a −80° C. freezer until HPLC analysis for acacetin content. Except for the double blanks, pentamethylquercetin (500 ng/mL) was used for concentration calibration. The analysis was carried out on a Waters HPLC system (Milford, Mass.) equipped with an Alltech column (C18, 250 mm×4.6 mm i.d., 5 µm, Grace, Deerfield, Ill.). The mobile phase consisted of 45% acetonitrile in 1% of acetic acid. The UV detector was set at a single wavelength of 260 nm. The lower limit of quantification was 50 ng/mL. The results indicated that the standard curve performance.

Ischemia-Reperfusion Model in Isolated Rat Hearts

Male SD rats (250-300 g) were anesthetized with phenobarbital (30 mg/kg, i.p.), and the heart were isolated and mounted to a Langendorff heart perfusion apparatus via the aorta and perfused with Krebs-Henseleit solution at 37° C. gassed with 95% $O_2$ and 5% $CO_2$. A saline-filled latex balloon connected by a polyethylene catheter to a pressure transducer was inserted into the left ventricle via an incision on the left atrium to measure left ventricular (LV) pressure. The balloon volume was adjusted and kept at a diastolic pressure of 0-5 mm Hg following insertion. ECG was recorded with two electrodes placed at the apex and the aorta. Signals were continuously monitored and stored on an IBM compatible PC computer using a multiple channels data acquisition system (Chengdu Instrument Ltd, Chendu, China).

A silk suture was placed around the left anterior descending artery (LAD) 2 mm distal to the left atrial appendage. A short length of polyethylene tube was placed over the suture on LAD as an occluder and the suture was pulled and the tube to ligate the coronary artery to induce regional ischemia. After a 20-min stabilization period, the hearts were treated by vehicle (DMSO control) or 0.3, 1, or 3 µM of the parent compound acacetin (0.3, 1, or 3 µM) for 10 min, and the LAD was ligated for 30-min. The ligation was released to allow for reperfusion for 2 h. Myocardial ischemia was confirmed by a decrease in left ventricular developed pressure and specific ST-T elevation on the ECG. At completing the reperfusion, the hearts were used to perform histological and/or molecular/biochemical analysis.

Hearts were excluded from the study if one of the following criteria was observed: (1) left ventricular developed pressure (LVP) was below 80 mmHg during baseline stabilization; (2) aortic wall was damaged during cannulation leading to a leakage during perfusion; or (3) hearts suffered from sustained irreversible arrhythmia during stabilization.

Determination of Myocardial Infarct Size

At the end of reperfusion, the LAD was re-ligated at the same location. The heart was infused with 0.5% Evans blue dye via the aorta to demarcate the perfused myocardium which became blue gradually. The heart was then frozen at −4° C. for 2-3 h and cut into 2-mm transverse slices. To identify the non-infarcted and infarcted areas, slices were incubated in 1% triphenyltetrazolium chloride (TTC) sodium phosphate buffer (pH 7.4) for 20 minutes at 37° C. and then immersed in 10% formalin to enhance the contrast between stained and unstained tissue. Photo images of the heart slices were taken and the size of area at risk and infarct area was measured by Image J software.

The myocardial ischemic risk area was identified as the region lacking blue staining and presented as a percentage of the total left ventricular (LV) area. Viable tissue in the risk area was stained deep red by TTC; the unstained area after TIC was the infarct tissue. Infarct area was expressed as a percentage of the total ischemic risk area.

Paraffin Embedded Tissue Section Preparation

To observe the histological changes of the ischemia-reperfusion hearts, the left ventricle was sectioned into 2-3 mm slices and drop-fixed in 10% formalin solution. After adequate fixation (a minimum 48 hours in room temperature), tissue slices were transferred into 70% ethanol for long term storage at 4° C. Tissue paraffin infiltration is processed in the tissue processor (Leica, Asp200s).

When the program was complete, tissue slices with cut side down were transferred into a mold with paraffin to form a block. The tissue block was placed on a microtome (Leica, RM2125/RT, Germany) and cut into ~5 µm slices. The tissue slices were float on the surface of 37° C. water bath until flat and then collected onto clean glass slides. Slides with paraffin sections were placed in a 65° C. oven for 20 minutes to bond the tissue to the glass. After then, slides were stored at room temperature for further treatment.

TUNEL Staining

Terminal deoxynucleotidyl transferase-mediated dUTP nick end labeling (TUNEL) staining of myocardial slices was performed to detect apoptosis in myocardium using the TUNEL Apoptosis detection kit (Genscript, Cat. No L00297, Piscataway, N.J., USA) according to the manufacturer's instructions. Briefly, 5 µM paraffin-embedded sections were dewaxed and rehydrated initially in a 60° C. oven for 30 minutes, then twice in xylene for five minutes each time and in gradient concentrations of ethanol (100%, 95%, 90%, 80%, 70%) for five minutes each time. The slides were then incubated with 0.1 M Citrate Buffer (pH 6.0) in a plastic jar and irradiated with 750 w for one minute. After the slides ere cooled to room temperature, the slides were transferred to the Blocking Solution for 30 minutes at 15-25° C. In the labeling procedure, 50 µL TUNEL Reaction Mixture was added to the samples and the slides were incubated for 60 minutes at 37° C. under wet conditions, protected from light. The slides were washed with PBS 3 times before 50 µL Streptavidin-HRP Solution was added to samples, which again were incubated under wet conditions at 37° C. protected from light for 30 minutes. To visualize the apoptosis cells, DAB-working solution was applied to the slides. The incubation time varied from 30 second to 5 minutes at room temperature. Samples were counterstained with haematoxylin prior to analysis by light microscope. Counterstaining aided in the morphological evaluation of normal and apoptotic nuclei, in which normal nuclei were stained as blue and apoptotic nuclei as brown. For quantitative analysis, TUNEL-positive cells in 10 different sectors with approximately 100-200 cells/sector were counted with high-power magnification, Axioskop 2 plus with software Axioversion (Axiovs 20v.4.8.2.0). Apoptotic cells were expressed as percentage of total cells in the field.

Western Blotting Analysis

For Western blotting analysis of different proteins, heart tissue samples from the ischemic zone were homogenized with an ice cold modified RIPA buffer. Protein concentration was determined using a Bio-Rad protein assay (Bio-Rad Laboratories, Hercules, Calif.). 50 µg proteins were mixed with sample buffer and denatured by heating to 95° C. for 5 min. Proteins were separated on a 10% SDS polyacrylamide gel and transferred to nitrocellulose membranes. Membranes were first blocked with 5% fat-free milk in 0.1% Tris-buffered saline with Tween (TTBS) for 2 hours and then probed with primary antibodies at 4° C. overnight. After TTBS washing 3 times, the membranes were incubated with secondary antibodies in TTBS at room temperature for 2 hours. Membranes were washed again with TTBS 3 times and then visualized on X-ray films using a chemo-luminescence detection system (ECL, GE Healthcare). In order to rule our differences in protein loading, the membranes were then stripped to probe the housekeeping protein GAPDH (Santa Cruz, Heidelberg, Germany). The intensities of target blots were measured by quantitative scanning densitometer image software (Image J). Target blots intensities in acacetin groups were normalized to the intensity of the same blot in vehicle group. The expression level of vehicle hearts was expressed as 1 and the relative intensities of target blots were used for quantitative and statistical analysis, Cell Line Culture HEK 293 cell line stably expressing the hKV1.5 gene (Wu et al., 2011) or hKv4.3 gene (Wu et al., 2013) was maintained in Dulbecco's modified eagle's medium (DMEM, Invitrogen, Hong Kong) supplemented with 10% fetal bovine serum and 400 µg/mL G418 in a 5% CO2 incubator. Cells were seeded on a glass cover slip for electrophysiology recording.

Rat Atrial Myocyte Preparation

Rat atrial myocytes were prepared with the procedure described previously (Li et al., 2002) with a slight modification. Briefly, After SD rats (250-300 g) were anesthetized with pentobarbital (30 mg/kg i.p.), the heart was mounted to a Langendorff heart perfusion apparatus via the aorta and perfused with HEPES-buffered Tyrode's solution at 37° C. gassed with 100% 02 for 5 min. The heart was perfused with $Ca^{2+}$-free Tyrode's solution for 5-8 min, followed by $Ca^{2+}$-free Tyrode's solution containing 0.06% collagenase (Type II, Worthington Biochemical, Lakewood, N.J., USA) and 0.1% bovine serum albumin (Sigma). When the heart became softened the left atrium was excised and placed in a high-K storage medium at room temperature for 2 h, and then used for electrophysiological recording (Li et al., 2002).

Electrophysiology Study

Ionic currents in HEK 293 cell lines and rat atrial myocytes were measured by the standard whole-cell patch-clamp technique using a standard pipette and bath solution with an EPC-10 amplifier and Pulse software (HEKA, Lambrecht, Germany). A 3M KCl-agar salt bridge was used as the reference electrode. The current signal was sampled at 5 kHz, recorded and stored in the hard disk of an IBM compatible computer. All experiments were conducted at room temperature (22-23° C.).

Statistical Analysis

Group data are expressed as mean±S.E.M. Nonlinear curve fitting was performed using Sigmaplot 8.0 (SPSS, Chicago, Ill.). Statistical analysis was performed using Student's t-test for paired or unpaired observations to evaluate significant differences between two group means, and ANOVA for multiple groups. Quantitative data were analyzed using the Fisher exact test. A two tailed P<0.05 was taken to indicate a statistical significant difference. Following are examples which illustrate the procedures of this invention. The examples should not be construed as limiting.

Example 1

Preparation of Water-Soluble Prodrugs of Acacetin

Synthesis of Prodrug A
Compound A-1

To an acetonitrile (35 mL) solution of acacetin (4 g, 14.1 mmol) was added 1.1 g of tetrazole (15.51 mmol) and 5.4 g of dibenzyl N,N-diisopropylphosphoramidite (15.51 mmol). After 12 h of stirring at room temperature, 9.75 mL of 70% of 1,1-dimethylethyl hydroperoxide in water was added and stirred for 5 min under room temperature. The mixture was extracted with 0.5M TBME/phosphate buffer (pH=7) and preparative HPLC was carried out by using 90% acetonitrile/10% $H_2O$. After evaporating the solvent, 5.8 g of yellow solid of compound A-1 was obtained.

Compound A-1: Yellow Solid. Yield 76%. $C_{30}H_{25}O_8P$ (544.49). EI-MS: m/z 545.14 [M]. $^1H$ NMR (400 MHz, $CDCl_3$): δ=12.81 (s, 1H), 7.83 (d, J=8.8 Hz, 2H), 7.03 (d, J=8.8 Hz, 2H), 6.84 (s, 1H), 6.62 (s, 1H), 6.54 (s, 1H), 5.19 (s, 2H), 5.17 (s, 2H), 3.91 (s, 3H) ppm.

Prodrug A

To a dichloromethane (40 mL) solution of 5.4 g of compound A-1 (9.9 mmol) was added 3.2 g of trimethylsilyl chloride (20.8 mmol). After stirring for 60 min at room temperature, the reaction mixture was evaporated and the crude product was dissolved in 2M TEAB buffer ($Et_3N$—$H_2CO_3$) and stirred for 15 min. The mixture was purified by HPLC by using 55% MeOH 50 mM TEAB without evaporation. The eluent was evaporated and washed by MeOH-L3.84 g of light yellow solid of compound A was obtained after drying.

Prodrug A: Light yellow solid. Yield 83%. $C_{16}H_{13}O_8P$·x $(C_6H_9N)$ [(364.24)·x(101.19)]. EI-MS: 567.1 [$C_{16}H_{13}O_8P$+ 2$(C_6H_9N)$]+. $^1H$ NMR (600 MHz, $CDCl_3$): δ=12.63 (s, 1H), 7.76 (d, J=8.76 Hz, 2H), 7.09 (s, 1H), 6.95 (d, J=8.76 Hz, 2H), 6.65 (s, 1H), 6.49 (s, 1H), 3.86 (s, 3H), 3.03-3.07 (m, 8H), 1.29-1.32 (t, 12H) ppm. The purified compound with >97%, has a higher solubility in Tris solution (pH=7.0, 10 mg/mL) than that of the parent compound acacetin (<0.2 µg/mL).

Synthesis of Prodrug B
Compound B-1

To a solution of acacetin (3 g, 10.5 mmol) and 4.5 mL of $NEt_3$ (32 mmol) in DMF (20 mL) at 0° C., 3.05 g of dibenzyl phosphite (11.6 mmol) in CCl4 (5.5 mL) was added dropwise and the mixture was stirred for 1 h at room temperature. The mixture was evaporated and the crude product was purified by column chromatography over silica gel by using n-hex/EtOAc/CH$_2$Cl$_2$ (6:1:2 v/v). After evaporating the solvent, 1.3 g of yellow solid of B-1 was obtained.

Compound B-1: Yellow Solid. Yield 54%. C$_{30}$H$_{25}$O$_8$P (544.49). EI-MS: m/z 545.14 [M]. $^1$H NMR (400 MHz, CDCl$_3$): δ=12.81 (s, 1H), 7.83 (d, J=8.8 Hz, 2H), 7.03 (d, J=8.8 Hz, 2H), 6.84 (s, 1H), 6.62 (s, 1H), 6.54 (s, 1H), 5.19 (s, 2H), 5.17 (s, 2H), 3.91 (s, 3H) ppm.

Compound B-2

To a solution of compound B-1 (2.1 g, 3.9 mmol) and formic acid (0.1 mL) in MeOH (20 mL) and THF (10 mL) was added 10% Pd/C (0.2 g) at 1 atm. After stirring for 4 h, Pd/C was filtered the filtrate was concentrated and 1.3 g of yellow solid of B-2 was obtained.

Compound B-2: Yellow Solid. Yield 92%. C$_6$H$_{13}$O$_8$P (364.24). EI-MS: m/z 365.04 [M$^+$], 285.07 [M+H—P(O)(OH)$_2$]$^+$. $^1$H NMR (400 MHz, DMSO-d$_6$): δ=12.91 (bs, 1H), 8.06 (d, J=8.8 Hz, 2H), 7.11 (d, J=8.8 Hz, 2H), 7.01 (s, 1H), 6.96 (s, 1H), 6.62 (s, 1H), 3.87 (s, 3H) ppm. $^{13}$C NMR (100 MHz, CDCl$_3$): δ 182.04, 163.74, 162.47, 161.15, 159.58, 156.54, 128.37, 122.74, 114.63, 106.05, 103.83, 102.64, 97.64, 55.55 ppm.

Prodrug B

B-2 was vigorously stirred in water (10 mL), 12 mL of 1M aq NaOH was slowly added, the mixture was stirred till most of B-2 was dissolved and the pH was 10. EtOH (25 mL) was added and light yellow solid was precipitated. The light yellow solid was filtered and washed with EtOH and dried yielding 0.6 g of light yellow solid Compound B was obtained.

Prodrug B: Light yellow solid. Yield 54%. C$_{16}$H$_{11}$O$_7$PNa$_2$ (408.21). EI-MS: m/z 387.04 [M+H—Na]$^+$. $^1$H NMR (400 MHz, DMSO-d$_6$): δ=12.90 (s, 1H), 8.04 (d, J=8.8 Hz, 2H), 7.10 (d, J=8.8 Hz, 2H), 7.02 (s, 1H), 6.98 (s, 1H), 6.60 (s, 1H), 3.89 (s, 3H) ppm. The purified compound with >99%, has a much higher solubility in H2O (25 mg/mL) than that of the parent compound acacetin (<0.1 µg/mL).

Synthesis of Prodrug C

Compound C-2

To a solution of acacetin (4.5 g, 15.8 mmol) in DMF (35 mL), 4.1 mL of chloromethyl ditertbutyl phosphate (20.6 mmol), 6.1 g of caesium carbonate (31.6 mmol) and 0.25 g of sodium iodide (0.1 eq) were added. After stirring the reaction mixture over night, the mixture was extracted with 0.5M TBME/phosphate buffer (pH=7) and preparative HPLC was carried out using 85% MeOH/15% H$_2$O. After evaporating the solvent, 4.1 g of a light yellow solid was obtained. 2.1 g of the yellow solid was dissolved in dichloromethane (35 mL) and 35 mL of tetrafluoroacetic acid was then added slowly. After stirring for 10 to 20 min, the reaction mixture was evaporated at low temperature. The crude product was washed with acetonitrile (30 mL) twice and was dried. 3.2 g of a light yellow solid of C2 was obtained.

Compound C-2: Light yellow solid. Yield 51%. C$_{17}$H$_{15}$O$_9$P (394.27). EI-MS: m/z 395 [M$^+$], 297 [M+H—OP(O)(OH)$_2$]$^+$. $^1$H NMR (200 MHz, DMSO-d$_6$): δ=12.8 (bs, 1H), 8.04 (d, J=9 Hz, 2H), 7.08 (d, J=9 Hz, 2H), 6.87 (s, 1H), 6.83 (d, J=6 Hz, 2H), 6.47 (d, J=3 Hz, 1H), 5.66 (s, 1H), 5.60 (s, 1H), 3.84 (s, 3H) ppm. $^{13}$C NMR (200 MHz, d$_6$-DMSO): δ=182.82, 164.57, 163.25, 162.72, 162.01, 157.69, 129.15, 123.31, 115.33, 106.40, 104.49, 100.08, 95.29, 87.96, 56.34 ppm $^{31}$P NMR (200 MHz, d$_6$-DMSO): δ=−1.56 ppm.

Prodrug C

To Compound C-2 (302 g, 8.1 mmol) dissolved in 10 mL deionized water, 34 mL of 0.25N NaOH (2 eq.) was added slowly (pH=7.02). The crude product was then lyophilized and 3.4 g of light orange solid Compound C was obtained.

Prodrug C: Light yellow solid. Yield 97%. C$_{14}$H$_{13}$O$_9$PNa$_2$ (438.23). EI-MS: 439.1 [M$^+$]. 1H NMR (200 MHz, D$_2$O):=7.53 (d, J=8.64 Hz, 2H), 6.67 (d, J=8.64 Hz, 2H), 6.60 (s, 1H), 6.30 (s, 1H), 6.28 (d, 1H), 5.43 (d, 2H), 3.67 (s, 3H) ppm. 13C NMR (200 MHz, D$_2$O): δ=162.35, 145.88, 145.10, 144.31, 141.96, 139.61, 113.73, 108.26, 101.56, 93.7, 91.37, 88.63, 84.71, 78.43 ppm. 31P NMR (200 MHz, D$_2$O): δ=2.69 ppm. The purified compound with >99%, has a much higher solubility in H$_2$O (25 mg/mL) than that of the parent compound acacetin (<0.1 g/mL).

Example 2

Figure 1B:
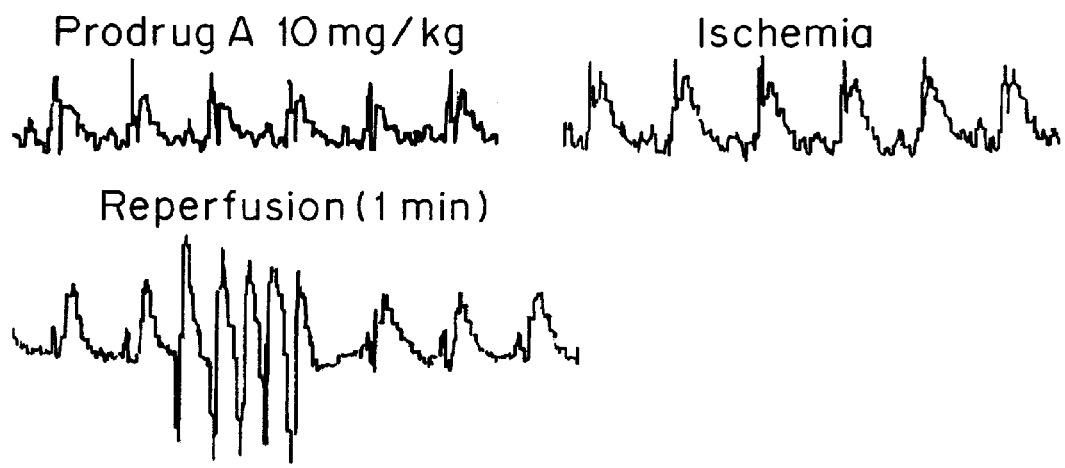
FIG. 1B is an ECG in a rat treated with prodrug A (10 mg/kg i.v. for 5 min) before ischemia, showing a brief ventricular tachycardia, then normal rhythm after reperfusion (reduced risk of sudden death).
Figure 1C:
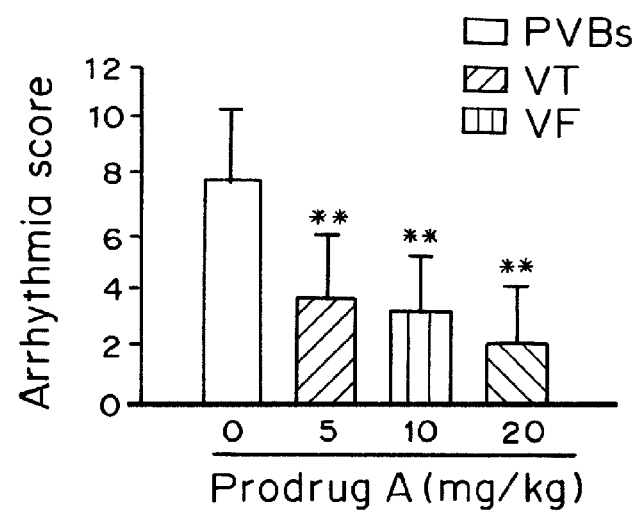
FIG. 1C is a graph showing arrhythmia score as a function of Prodrug A concentration.
Figure 1D:
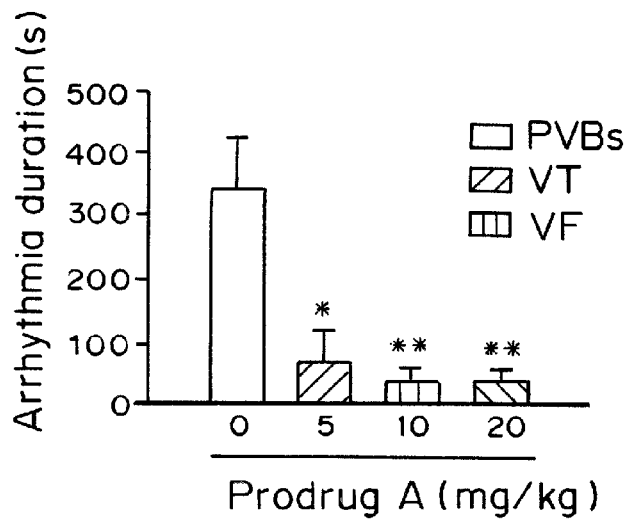
FIG. 1D is a graph showing arrhythmia duration as a function of Prodrug A concentration.
Figure 1E:
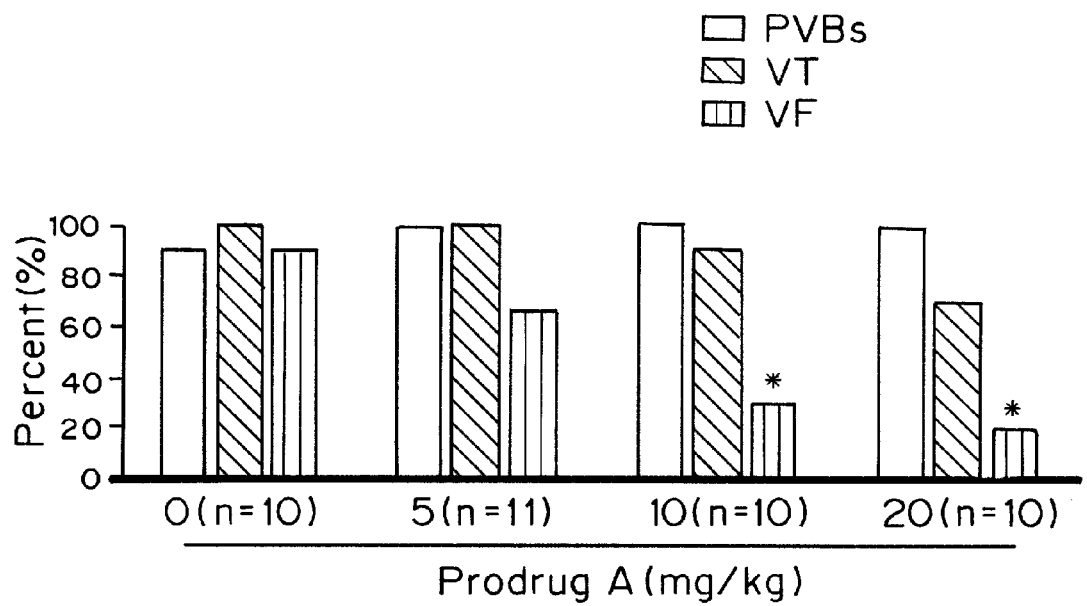
FIG. 1E is a graph showing percent PVBs, VT, and Vf as a function of Prodrug A concentration.

Cardioprotection of Water-Soluble Prodrug A Against Ventricular Arrhythmias Induced by Ischemia-Reperfusion Injury in an Anesthetized Rat Model To investigate the effects of water-soluble Prodrug A on ventricular arrhythmias induced by ischemia-reperfusion injury, the in vivo ischemia-reperfusion model was established in SD rats. In this model, the animal, ventricular arrhythmias, including premature ventricular beats (PVBs), and ventricular tachycardia (VT), were developed with 10 min ischemia (ligation of coronary anterior descending artery) followed by 10 min reperfusion. Ventricular fibrillation was frequently observed during the early reperfusion in the control animal with intravenous vehicle (FIG. 1A), but not in the animal treated with intravenous Prodrug A (10 mg/kg for 5 min, FIG. 1B). Prodrug A at 5 mg, 10, and 20 mg/kg decreased arrhythmia score (FIG. 1C) and arrhythmia duration in a dose-dependent manner (P<0.05 or P<0.01 vs. vehicle). Importantly, incidence of severe ventricular fibrillation was significantly reduced by 10 mg or 20 mg/kg Prodrug A (P<0.05, 90% in vehicle vs. 30% or 20% in Prodrug A).

Figure 2A:
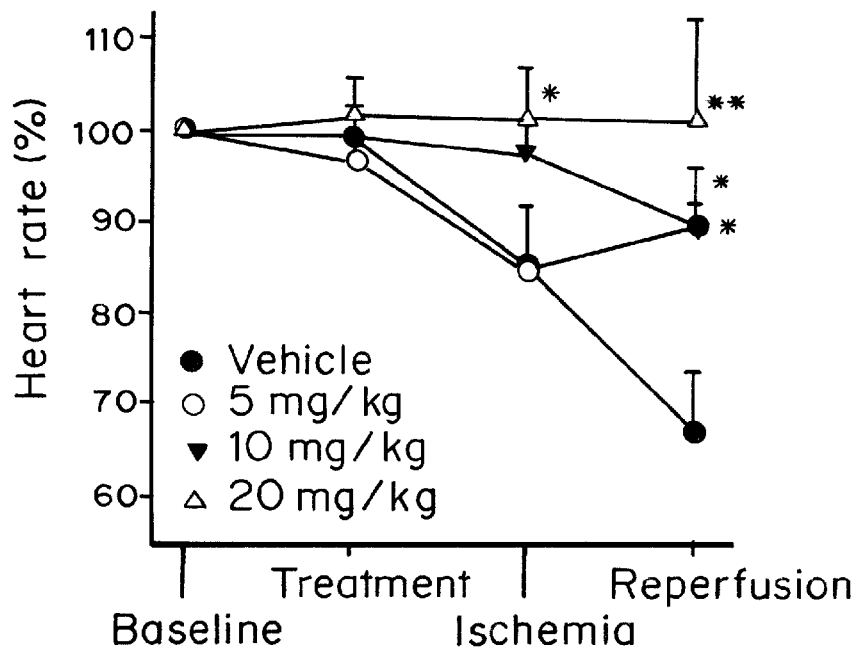
FIG. 2A is a graph showing the change in heart rate (%) at different time points as a function of Prodrug A concentration.
Figure 2B:
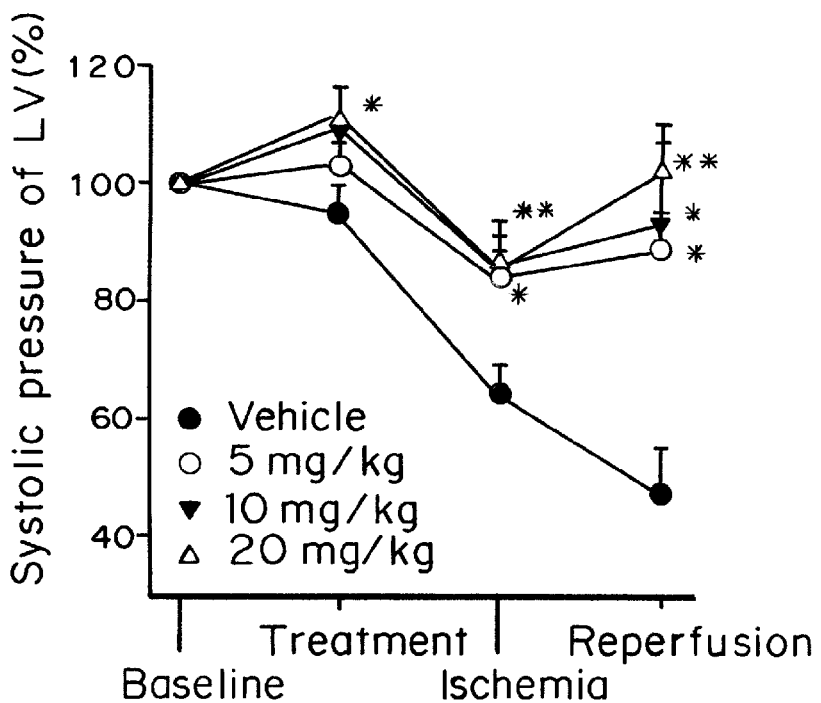
FIG. 2B is a graph showing the change in systolic pressure of LV (%) at different time points as a function of Prodrug A concentration.
Figure 2C:
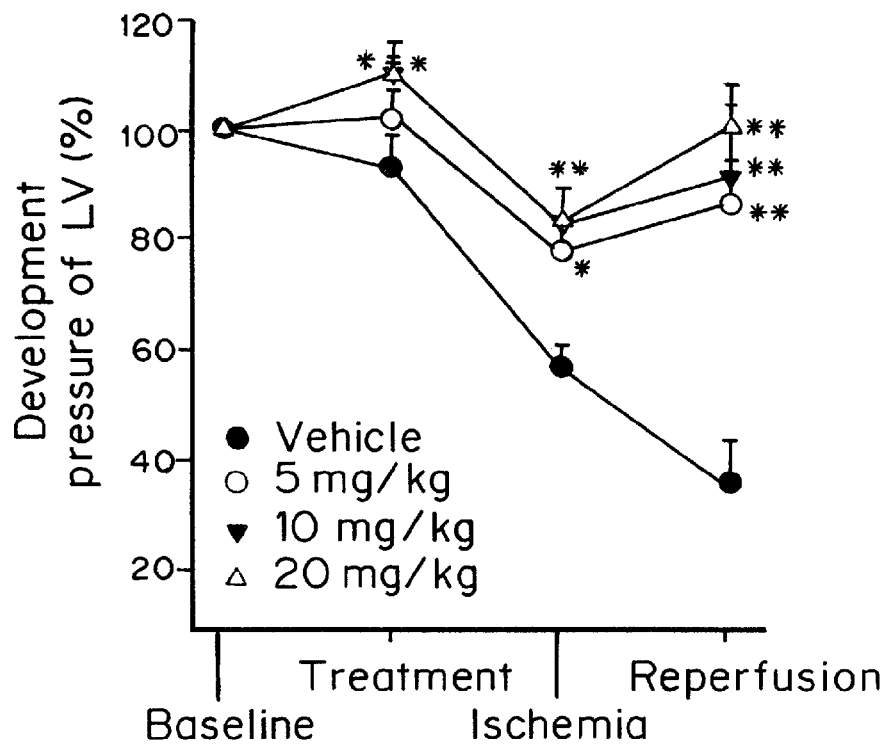
FIG. 2C is a graph showing the change in development pressure of LV (%) at different time points as a function of Prodrug A concentration.
Figure 2D:
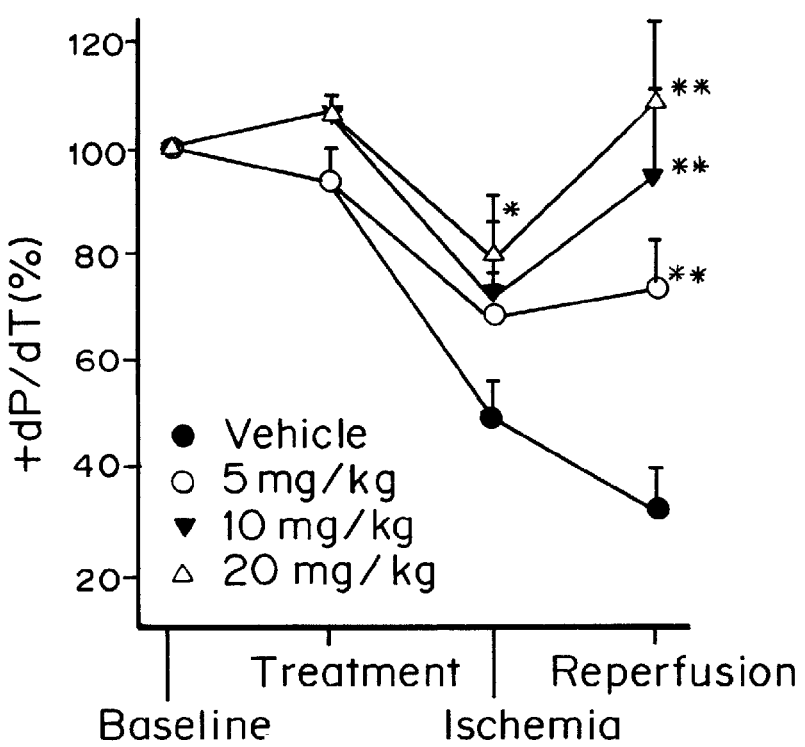
FIG. 2D is a graph showing the change +dP/dT (%) at different time points as a function of Prodrug A concentration. (n=10-11 experiments, *P<0.05, P<0.01 vs. vehicle).

In addition to the anti-ventricular fibrillation, Prodrug A prevented heart rate reduction (FIG. 2A), and improved the decreased function contractile function including left ventricular systolic pressure (FIG. 2B), development pressure (FIG. 2C), and +dP/dT (FIG. 2D) induced by ischemia and/or reperfusion injury in a dose-dependent manner (P<0.05 or P<0.01 vs. vehicle). These results indicate that the water-soluble prodrug is effective in anti-ventricular arrhythmias and preserving heart function in in vivo ischemia-reperfusion rat model, suggesting a potential application of the prodrug in rescuing myocardial infarction induced by ischemia-reperfusion injury.

Figure 2E:
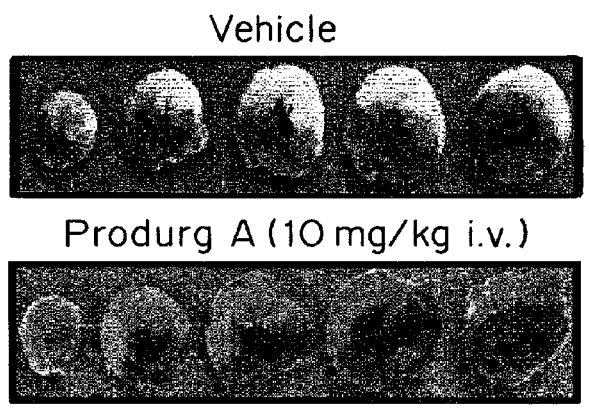
FIG. 2E displays the ventricular slices of the heart with the TCC-staining from anesthetized rats, showing that the infarct area is reduced in the animal treated with prodrug A (n=4, P<0.01 vs vehicle).
Figure 2E:
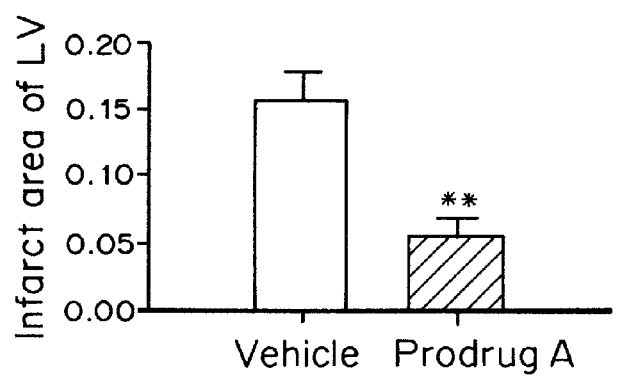

On the other hand, before the coronary artery ligation the prodrug at 10 mg and 20 mg/kg slightly but significantly increased the left ventricular systolic pressure (FIG. 2B) and development pressure (FIG. 2C) without affecting heart rate. This indicates that inhibition of L-type Ca2+ channels, which may reduce heart contractile function, is not involved in the cardioprotection of prodrug A. Its cardioprotection is involved in the anti-myocardial infarction (FIG. 2E).

Example 3

Ex Vivo Pharmacological Activity of the Water-Soluble Prodrug

Figure 3G:
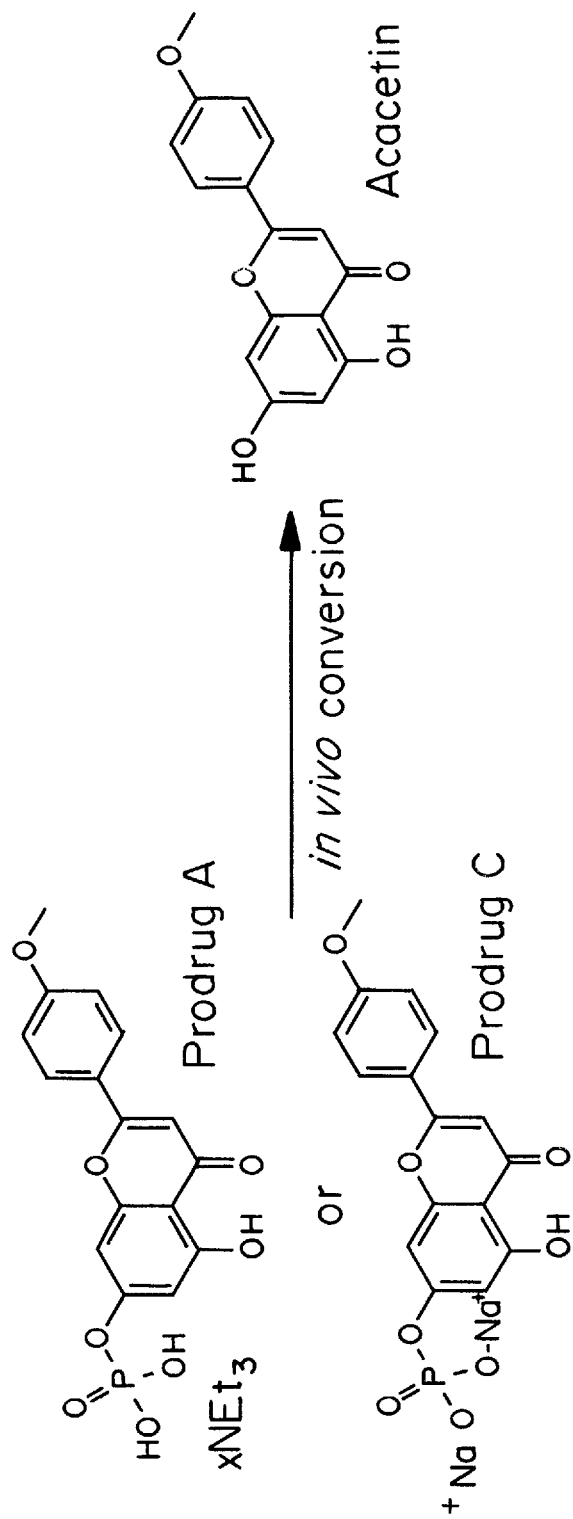
FIG. 3G shows the predicted in vivo conversion of the prodrugs into the parent compound acacetin.

To determine whether acacetin prodrugs are pharmacologically inactive in vitro, Kv1.5 current and Kv4.3 current were recorded in HEK 293 cell lines and IKACh was activated in rat atrial myocytes. Prodrug A at 30 µM had no inhibitory effect Kv1.5 current (FIG. 3A), Kv4.3 current (FIG. 3B) or IKACh (FIG. 3C) in representative cells, consistent with the previous reports for other prodrugs. However, Kv1.5 current (FIG. 3D), Kv4.3 current (FIG. 3E) or IKACh (FIG. 3F) was inhibited by 10 µM acacetin in representative cells consistent with experimental reports. Similarly, water-soluble Prodrug B and prodrug C of acacetin had no inhibitory effect on Kv1.5 current, Kv4.3 current or IKACh (Data not shown). These results indicate that the in vivo conversion of the prodrug is involved in cardioprotection.

Example 4

In Vivo Conversion of Water-Soluble Prodrugs

Figure 4A:
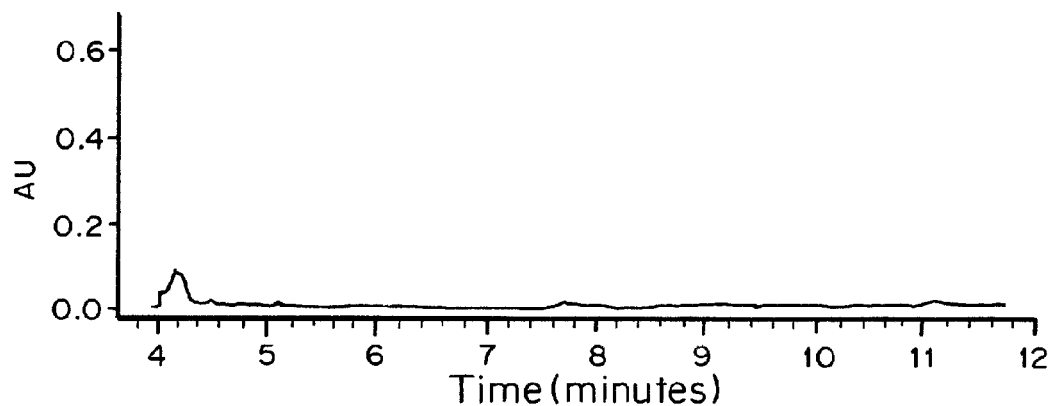
FIG. 4A is an HPLC trace of a blood sample before administration of Prodrug A.
Figure 4B:
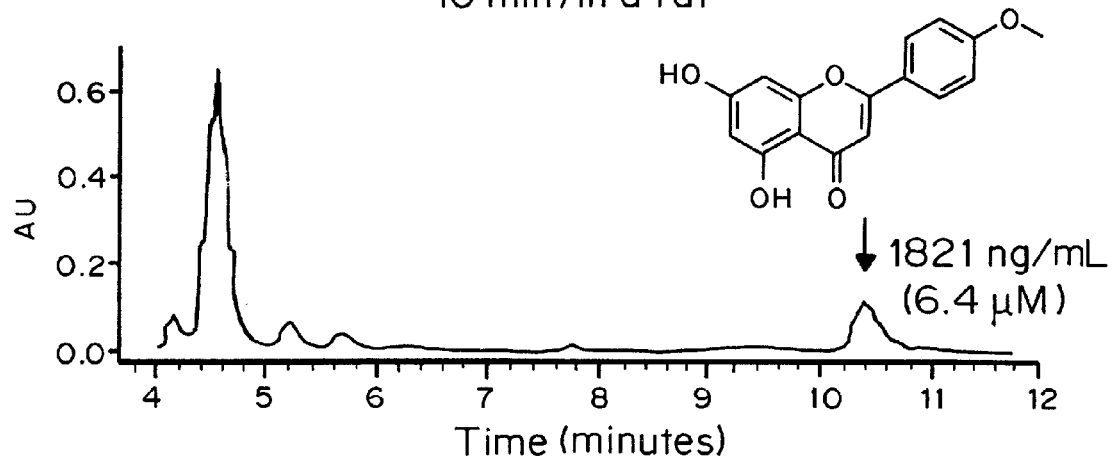
FIG. 4B is an HPLC trace of a blood sample after i.v. administration of 20 mg/kg Prodrug A.

The in vivo conversion of water-soluble prodrug A was determined in anesthetized SD rats. Prodrug A (20 mg/kg i.v.) was infused for 30-60 min, and levels of the parent compound acacetin in blood plasma were determined by HPLC analysis. FIG. 4 shows that HPLC peaks was observed for the parent compound only after infusion of Prodrug A. The parent compound converted from the prodrug A reached a concentration of 6.4 µM. The results for in vivo conversion for Prodrug A, Prodrug B, and Prodrug C at different time-points showed that the concentrations of acacetin can reach therapeutic concentrations.

Example 5

Figure 5C:
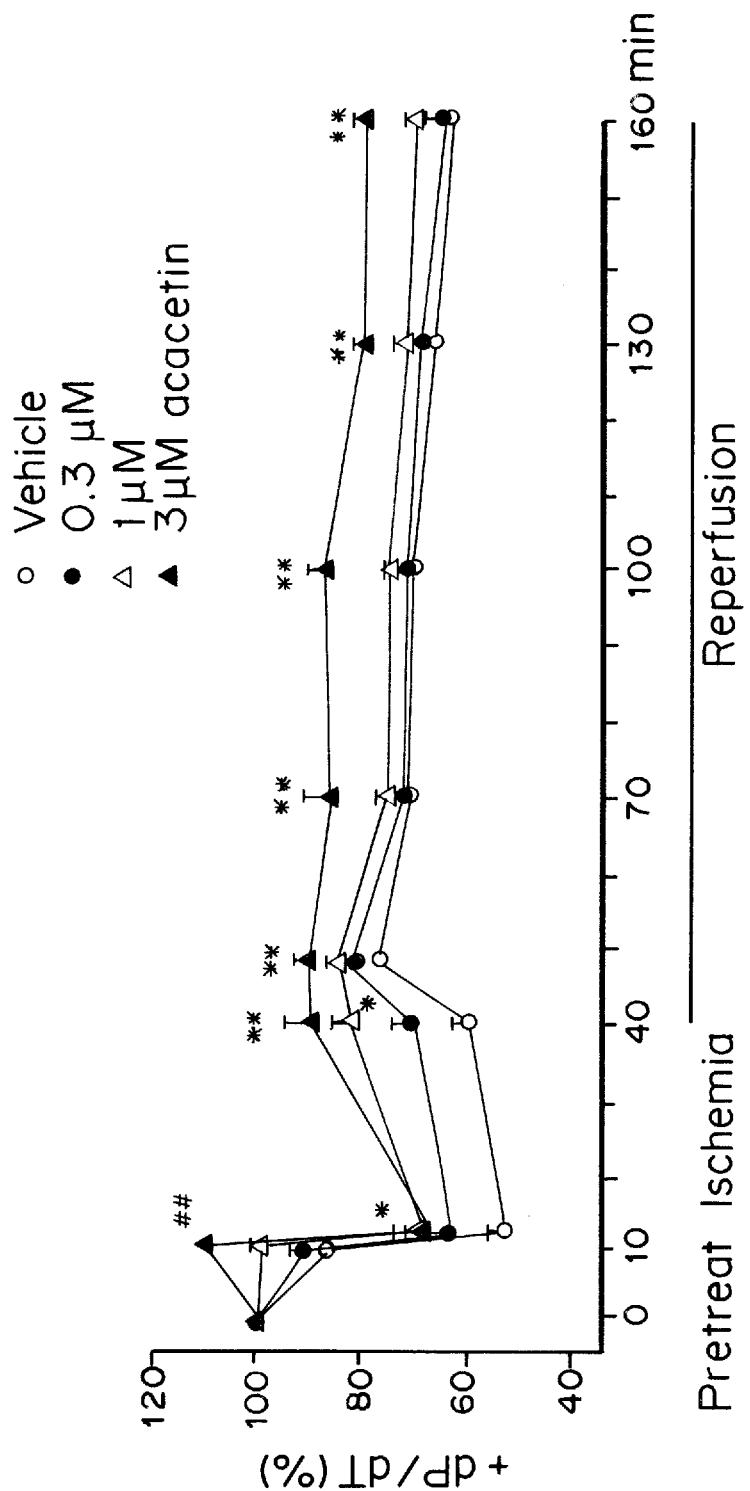
FIG. 5C is a graph showing the effect of acacetin concentration on +dP/dT (%) as a function of time. All experiments n=10-12, #<0.05, ##P<0.01 vs. 0 min; *P<0.05, **P<0.01 vs. vehicle.

Ex Vivo Cardioprotection of the Parent Compound Against Ischemia-Reperfusion Injury To determine the mechanisms of cardioprotection, the ischemia-reperfusion model was established in isolated rat hearts using accurate concentrations of the parent compound acacetin. The hearts perfused with the Langendorff system were exposed to 30 min ischemia (coronary ligation) followed by 120 min reperfusion (FIG. 5). After a 20 min stabilization period, the heart was treated with 0.3, 1, 3 µM acacetin, or equivolume vehicle (DMSO) for 10 min and then 30 min during ischemia.

Acacetin at 0.3, 1, 3 µM significantly increased the coronary flow rate to 108.9±2.3%, 122.1±4.9%, 125.8±6.6%, respectively versus control (n=10-12, P<0.05 or P<0.01 vs control) before ischemia, while vehicle had no such effect (FIG. 5A). Acacetin at 3 LM improved the reduced coronary flow rate induced not only by ischemia, but also by reperfusion (FIG. 5A, P<0.01 vs. vehicle with 16-25% difference). The increase in coronary flow rate may be an important mechanism for the cardioprotection observed with intravenous prodrug in anesthetized rats.

Acacetin at 3 µM also significantly increased the heart contractile function (i.e. left ventricular systolic pressure and +dP/dT) by around 10% of control (FIGS. 5B and 5C, n=10, P<0.01 vs control) before ischemia. Importantly, acacetin at 3 µM significantly prevented the decrease of heart contractile function induced by ischemia-reperfusion (FIGS. 5B and 5C, P<0.01 vs. vehicle, with 15-20% difference). These results indicate that cardioprotection observed in vivo with acacetin Prodrug A and in perfused hearts is most likely related at least in part to the increase in coronary flow rate by acacetin.

Figure 6A:
FIG. 6A displays the ventricular slices of the heart with the TCC-staining showing significant infarct area in a vehicle control heart.
Figure 6B:
FIG. 6B displays the ventricular slices exhibiting the reduced infarct area in the heart with 3 μM acacetin treatment (40 min).
Figure 6C:
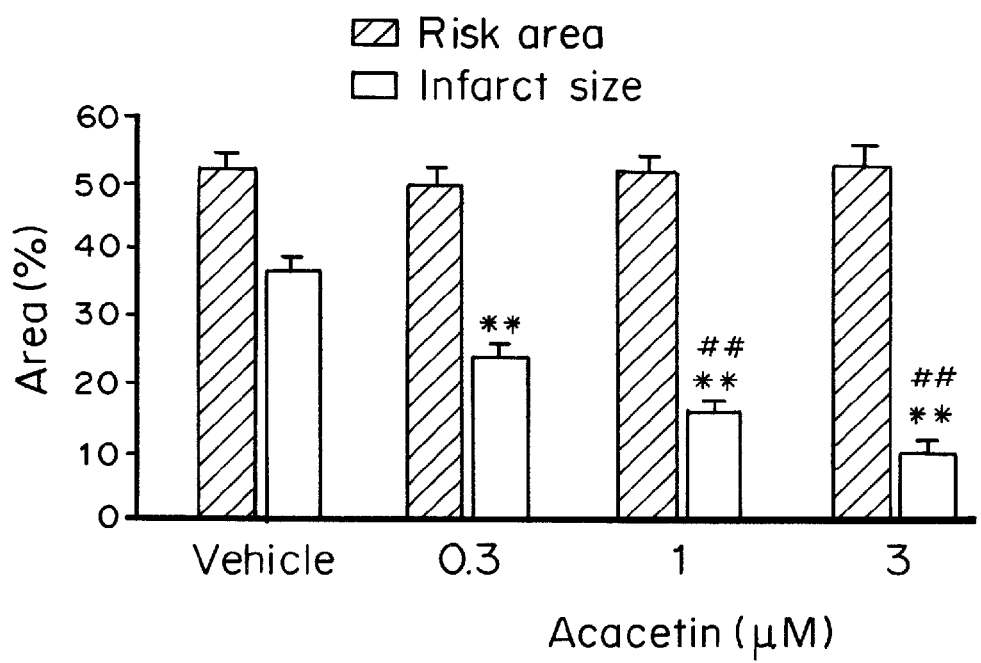
FIG. 6C is a graph showing the mean percentage of risk area and infarct area of the ventricles with ischemia-reperfusion injury, showing reduction of infarct area in hearts treated with 0.3, 1, or 3 μM in a concentration-dependent manner (n=10-12 experiments, <0.01 vs. vehicle; ##P<0.01 vs. 0.3 or 1 μM acacetin).

The infarct area was assessed by TTC staining in myocardial slices, which shows remarkable infarct size in the heart treated with vehicle (FIG. 6A), and is reduced in the heart treated with 3 µM acacetin (FIG. 6B). The mean percentage value of the infarct area induced by ischemia-reperfusion injury was significantly decreased by 0.3, 1, and 3 µM acacetin in a concentration-dependent manner (FIG. 6C, P<0.01 vs.

vehicle). The significant reduction of infarct size was observed at low concentration of 0.3 µM acacetin, indicating in addition to the increase of coronary flow rate, other mechanisms, e.g. anti-apoptosis, anti-oxidation, and anti-inflammation may also be involved in its cardioprotection.

Example 6

Mechanism of Cardioprotection Against Myocardial Infarction

Figure 6D:
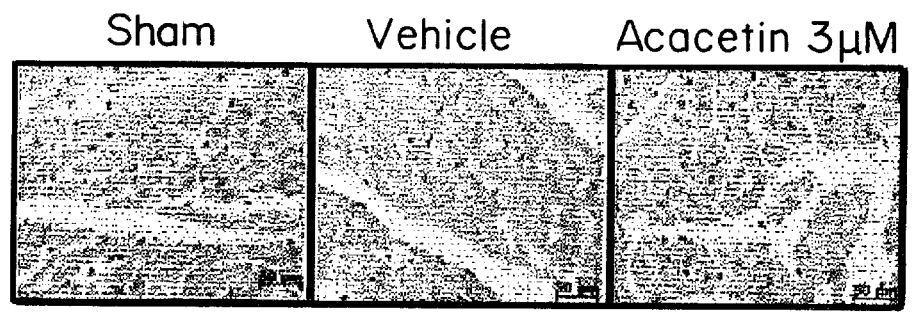
FIG. 6D is an image of HE-stained slices showing myocardial damage in vehicle-treated heart, but not in acacetin-treated heart.
Figure 6E:
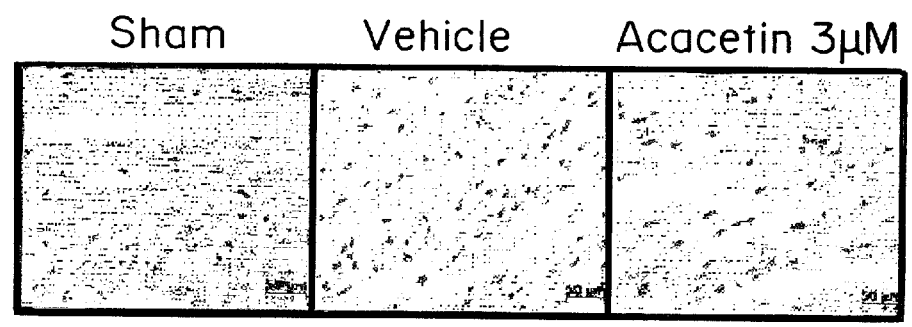
FIG. 6E is an image of TUNEL-stained slices.
Figure 6F:
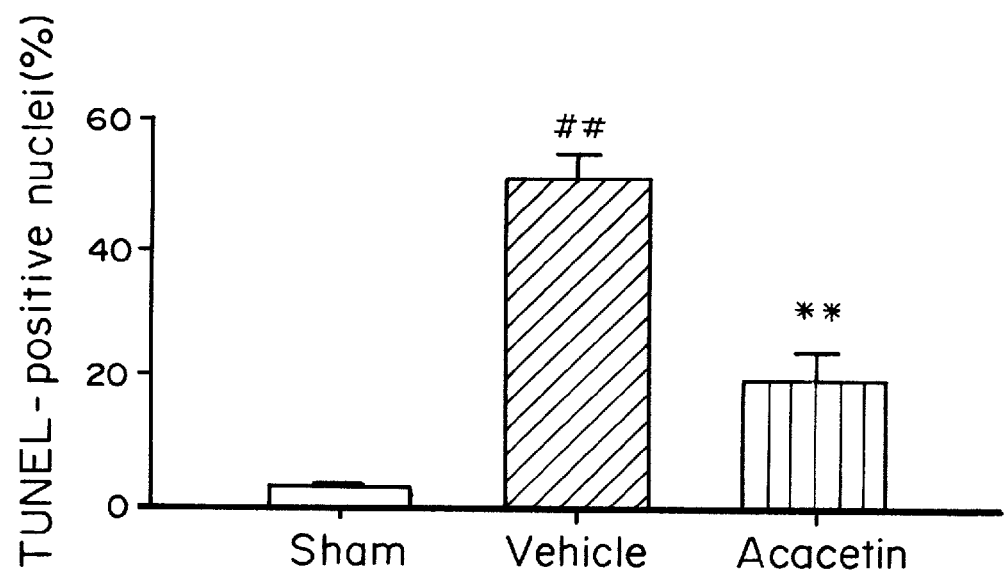
FIG. 6F is a graph showing the mean apoptosis cell number with dark-brown nuclei in hearts treated with vehicle or 3 μM acacetin (n=5 experiments, P<0.01, vs. sham; ##P<0.01 vs. vehicle).

The cardioprotection against myocardial infarction of acacetin may involve anti-apoptosis. FIGS. 6D and 6E are images of HE- and TUNEL-stain in myocardial slices. The number of TUNEL-positive nuclei was counted, and the percentage cell number with TUNEL-positive nuclei (FIG. 6F) shows that ischemia-reperfusion caused significant increase of myocyte apoptosis and acacetin at 3 µM acacetin decreased the TUNEL-positive nuclei from 51.1±3.8% (n=5, vs vehicle control) to 20.2±4.1% (n=5, P<0.01 vs. vehicle), indicating significant anti-apoptosis.

Figure 7A:
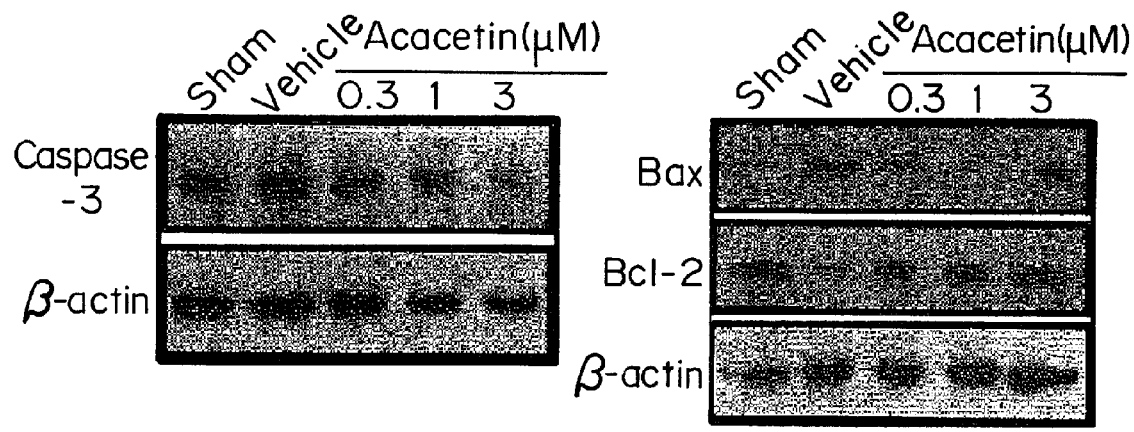
FIG. 7A are Western blots for expression of caspase-3, Bax, and Bcl-2 in the absence and presence of 0.3, 1, and 3 μM acacetin.
Figure 7B:
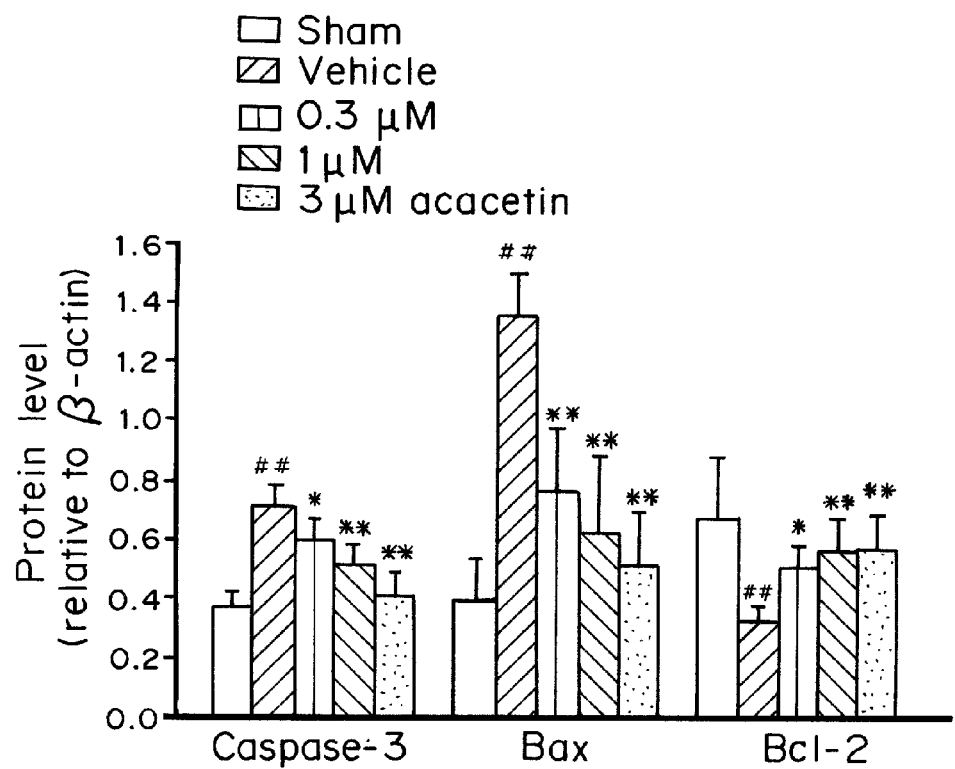
FIG. 7B is a graph showing protein level (relative to β-actin) for Caspase-3, Bax, and Bcl-2 as a function of acacetin concentration (n=4 experiments, *P<0.05, **P<0.01 vs. vehicle).

Further the molecular mechanism of anti-apoptosis of the prodrugs and the parent compound was determined for expression of the pro-apoptotic proteins caspase-3, and Bax (Bcl-2-associated X), and the anti-apoptotic protein Bcl-xL (B-cell lymphoma-extra large) in ischemia/reperfused myocardium treated with vehicle, 0.3, 1, or 3 acacetin. Acacetin decreased the expression of caspase-3 and Bax, while increased the expression of Bcl-2 (FIG. 7A). The relative expression levels of these proteins are illustrated in FIG. 7B in vehicle group (n=4) and acacetin (0.3, 1, and 3 µM) groups (n=4 for each group). Acacetin increased the anti-apoptotic molecule Bcl-2, and decreased the pro-apoptotic molecules Bax and caspase-3 in a concentration-dependent manner (P<0.05 or P<0.01 vs. vehicle).

Figure 7C:
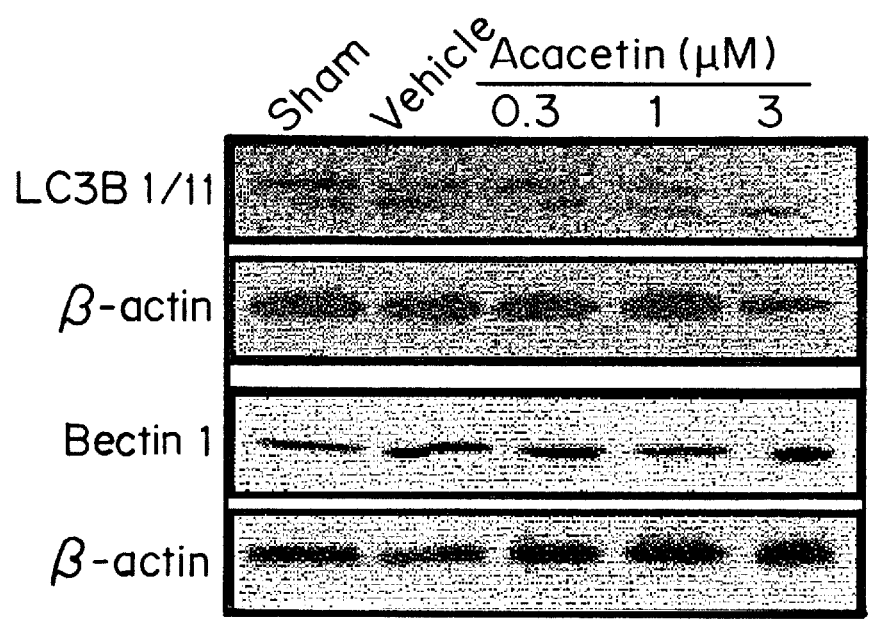
FIG. 7C are Western blots for the expression of autophagy proteins LC3B I/II and Beclin 1.
Figure 7D:
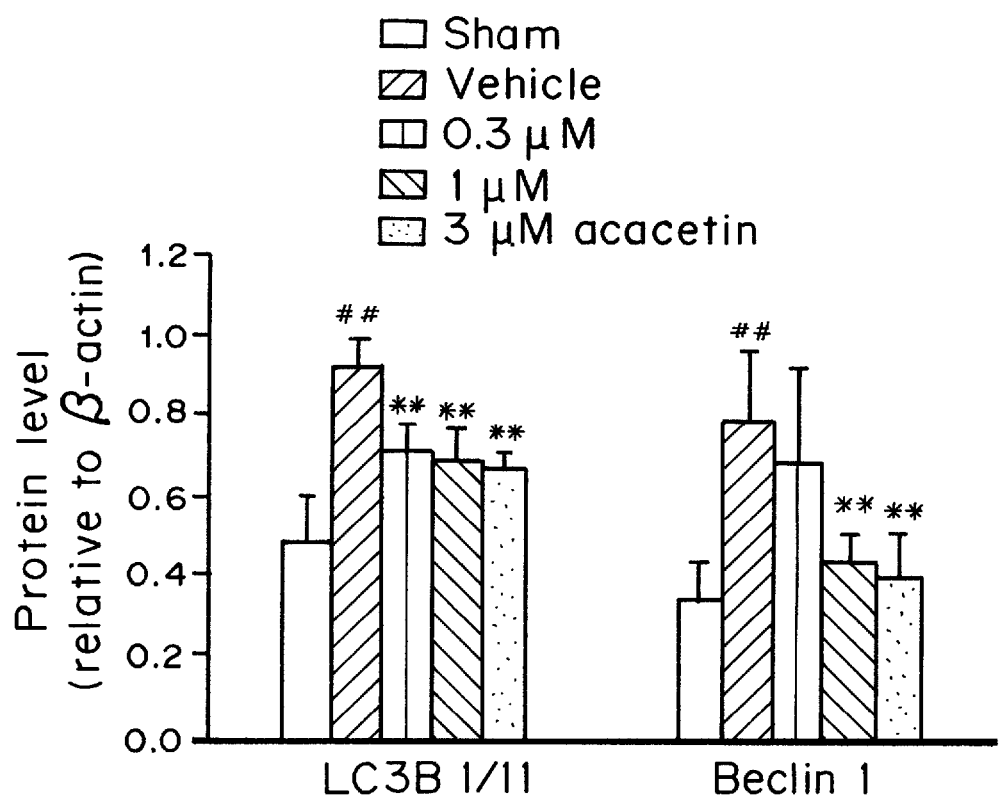
FIG. 7D is a graph showing protein level (relative to β-actin) for LC3B I/II and Beclin 1 as a function of acacetin concentration (n=4, ##P<0.01 vs. Sham; *P<0.05, **P<0.01 vs. vehicle).

The cardioprotection against myocardial infarction of acacetin probably involve anti-autophagy. Increase of myocardial autophagy is indicated by evaluating BLC3 I/II and beclin 1 protein level, which is reversed by acacetin treatment in a concentration-dependent manner (FIGS. 7C and 7D).

Figure 8A:
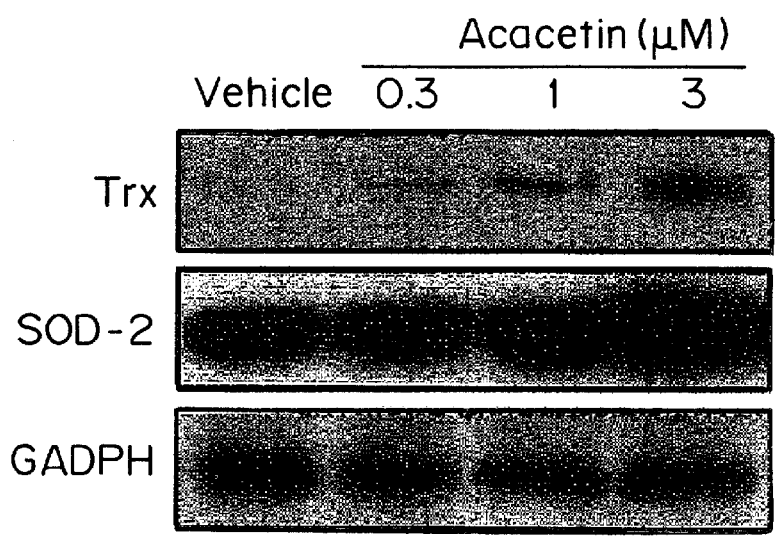
FIG. 8A are Western blots for expression of the oxidation proteins thioredoxin (Trx) and superoxide dismutase 2 (SOD-2).
Figure 8B:
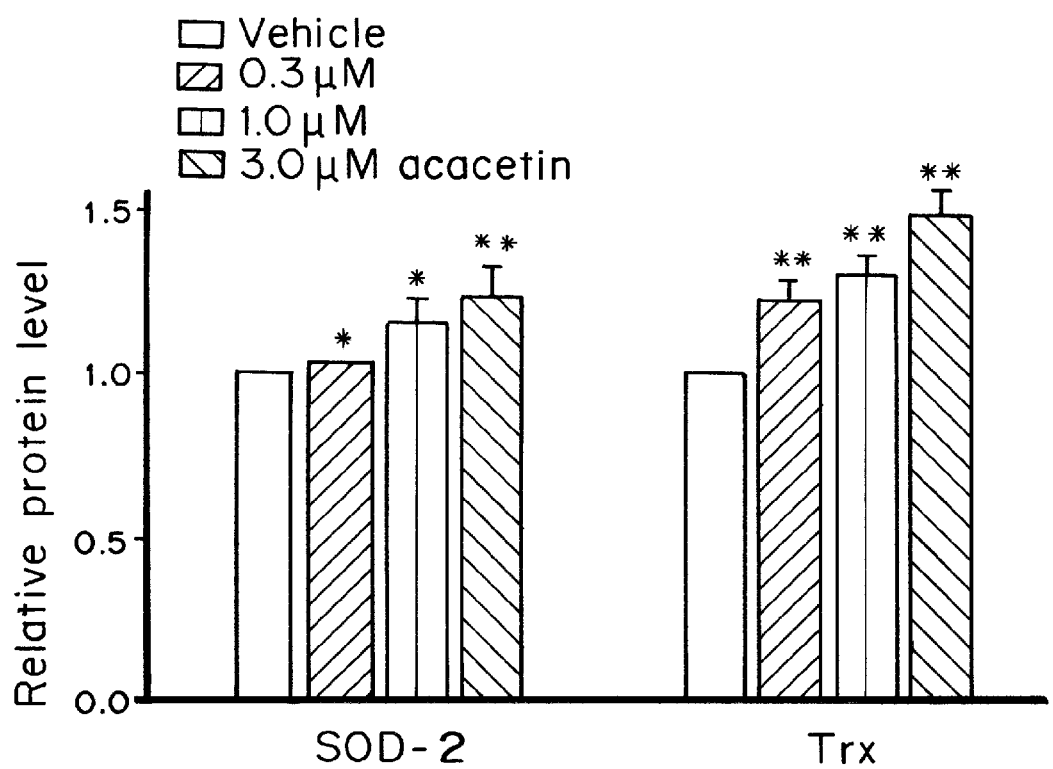
FIG. 8B is a graph showing relative protein level for SOD-2 and Trx as a function of acacetin concentration.

The cardioprotection against myocardial infarction of acacetin probably involve anti-oxidant stress. The anti-oxidation stress proteins Trx (thioredoxin) and SOD-2 (superoxide dismutase 2) were determined in ischemia/reperfused myocardium treated with or without acacetin treatment. Trx interacts with other proteins to regenerate proteins damaged by reactive oxygen species (ROS) through a redox-active cysteine pair, while SOD-2 is a ubiquitous enzyme with an essential function in protecting aerobic cells against oxidative stress. Western blots (FIG. 8A) show the expression of SOD-2 and Trx was increased by acacetin. The mean relative levels of Trx SOD-2 were upregulated by acacetin in a concentration-dependent manner (FIG. 8B).

Figure 8C:
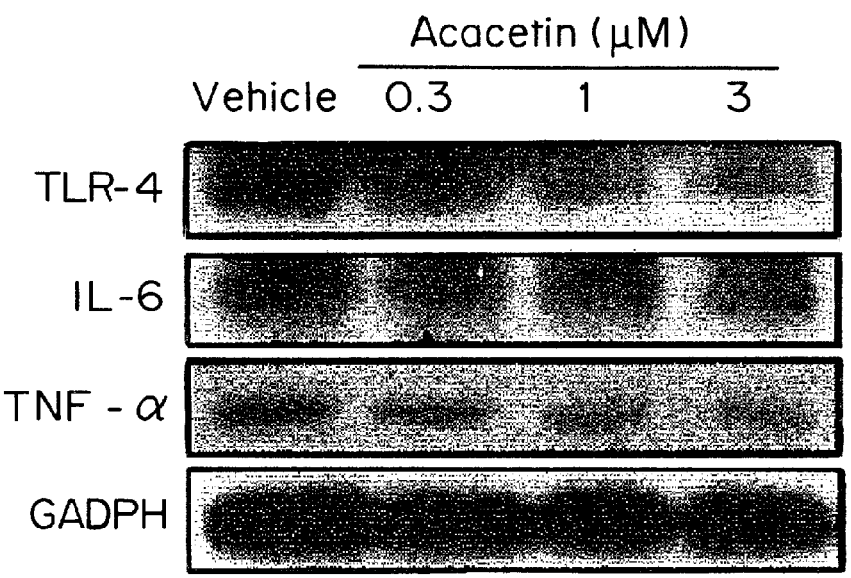
FIG. 8C are Western blots for expression of the pro-inflammatory cytokines toll-like receptor-4 (TLR-4), interleukin-6 (IL-6), tumor necrosis factor-α (TNF-α) in rat left ventricles with ischemia-reperfusion injury in the absence and presence of 0.3, 1, and 3 μM acacetin.
Figure 8D:
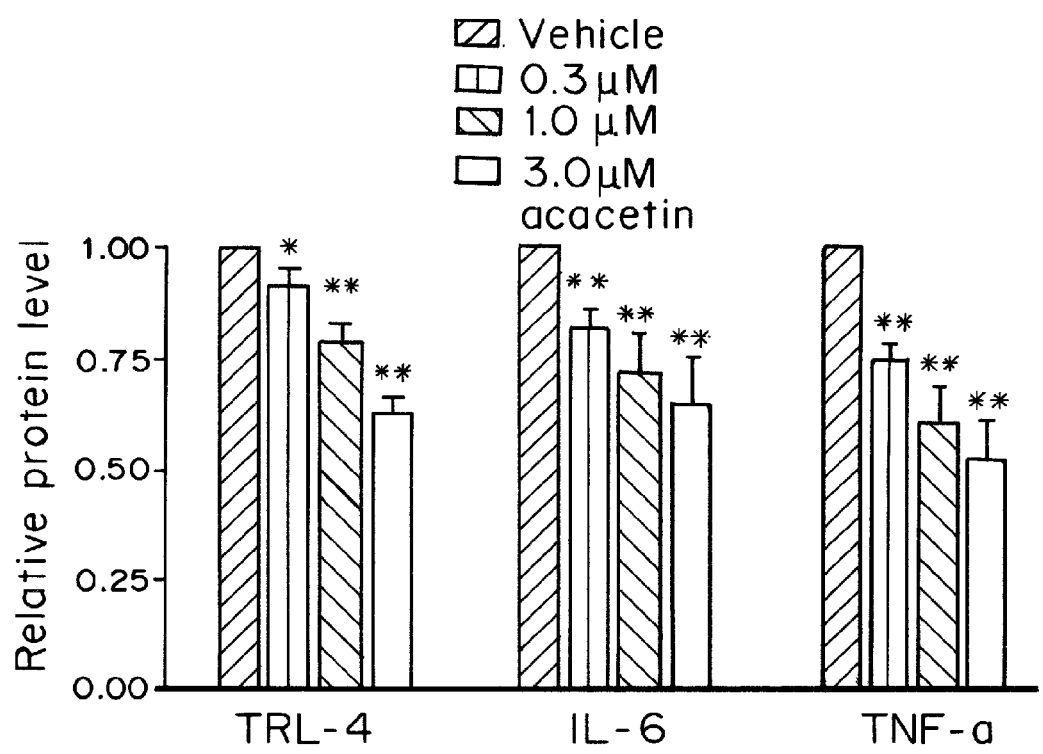
FIG. 8D is a graph showing relative protein level for TLR-4, IL-6, and TNF-α as a function of acacetin concentration (n=5-6 experiments, *P<0.05, **P<0.01 vs. vehicle).

The cardioprotection against myocardial infarction of acacetin likely also involves anti-inflammation. Inflammation plays an important role in mediating and exacerbating myocardial ischemia-reperfusion injury. FIGS. 8C and 8D show that expression of inflammation indicators TLR-4, IL-6, and TNF-α were reduced in myocardial tissues treated with acacetin in a concentration-dependent manner.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula I:

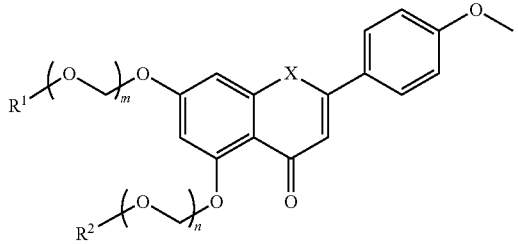

wherein:
- m and n are independently an integer from 0 to 3;
- X is O or N or S;
- $R^1$ is selected from the group consisting of alkenyl, alkynyl, cycloalkyl, cycloalkenyl, cycloalkynyl, heterocyclyl, aryl, alkaryl, arylalkyl, carboxyalkyl, amino, aminoalkyl, alkylamino, dialkylamino, arylamino, diarylamino, alkylarylamino, hydroxyalkyl, alkoxyalkyl, $PO_3H_2$, $PO_3^{2-}M$, where M is one or more ammonium ions, alkali metal ions, or alkaline earth metal ions, phosphate ester, $SO_3H$, $SO_3^-M$, where M is an ammonium ion, alkali metal ion, or alkaline earth metal ion, sulfonic ester, sulfonic ester, sulfonamide, —C(=O)-$A^1$, and —C(=O)-L-$A^2$; wherein $A^1$ and $A^2$ are independently halo, hydroxy, thiol, alkenyl, alkynyl, cycloalkyl, cycloalkenyl, cycloalkynyl, alkaryl, arylalkyl, carbamate, amino, alkylamino, arylamino, dialkylamino, alkylarylamino, diarylamino, sulfonamide, heteroalkyl; wherein L is alkylene, alkenylene, alkynylene, aralkylene or alkarylene; and
- $R^2$ is selected from the group consisting of hydrogen, alkyl, alkenyl, alkynyl, cycloalkyl, cycloalkenyl, cycloalkynyl, heterocyclyl, aryl, alkaryl, arylalkyl, carboxyalkyl, amino, aminoalkyl, alkylamino, dialkylamino, arylamino, diarylamino, alkylarylamino, hydroxyalkyl, alkoxyalkyl, $PO_3H_2$, $PO_3^{2-}M$, where M is one or more ammonium ions, alkali metal ions, or alkaline earth metal ions, phosphate ester, $SO_3H$, $SO_3^-M$, where M is an ammonium ion, alkali metal ion, or alkaline earth metal ion, sulfonic ester, sulfonic ester, sulfonamide, —C(=O)-$A^1$, and —C(=O)-L-$A^2$; wherein $A^1$ and $A^2$ are independently hydrogen, halo, alkoxy, hydroxy, thiol, alkyl, alkenyl, alkynyl cycloalkyl, cycloalkenyl, cycloalkynyl, alkaryl, arylalkyl, carbamate, amino, alkylamino, arylamino, dialkylamino, alkylarylamino, diarylamino, sulfonamide, heteroalkyl; wherein L is alkylene, alkenylene, alkynylene, arylene, aralkylene or alkarylene;

or a pharmaceutically acceptable salt thereof.

2. The compound of claim 1, having formula IIA:

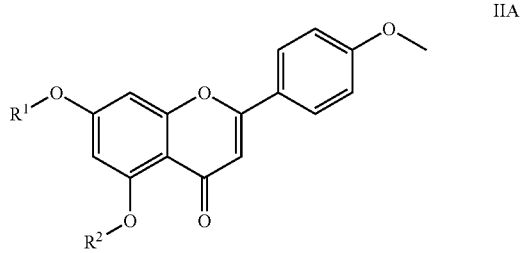

wherein:
- X=O; m=0; n=0;
- $R^1$ is selected from the group consisting of $PO_3H_2$, $PO_3^{2-}M$, wherein M is one or more ammonium ions, alkali metal ions, or alkaline earth metal ions, phosphate ester, sulfonic ester and sulfonamide; and
- $R^2$ is selected from the group consisting of hydrogen, $PO_3H_2$, $PO_3^{2-}M$, wherein M is one or more ammonium ions, alkali metal ions, or alkaline earth metal ions, phosphate ester, sulfonic ester and sulfonamide;
- wherein if $R^2$ is H, $R^1$ is not sulfonate.

3. The compound of claim 1, having formula IIB:

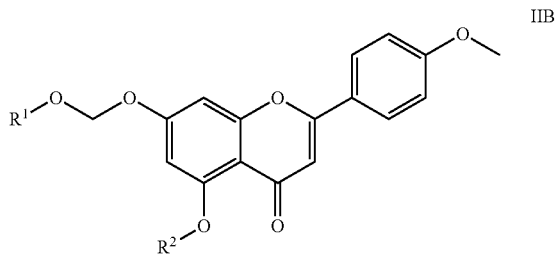

wherein:
- X=O; m=1; n=0;
- $R^1$ is selected from the group consisting of $PO_3H_2$, $PO_3^{2-}M$, wherein M is one or more ammonium ions, alkali metal ions, or alkaline earth metal ions, phosphate ester, sulfonate with ammonium or alkali or alkaline earth metal ions, sulfonic ester and sulfonamide; and
- $R^2$ is selected from the group consisting of hydrogen, $PO_3H_2$, $PO_3^{2-}M$, wherein M is one or more ammonium ions, alkali metal ions, or alkaline earth metal ions, phosphate ester, sulfonate with ammonium or alkali or alkaline earth metal ions, sulfonic ester and sulfonamide.

4. The compound of claim 1 having the structure:

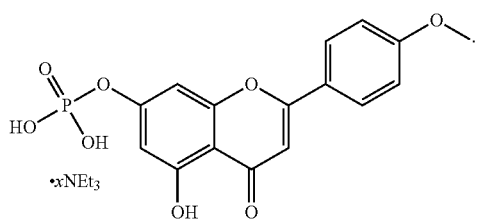

5. The compound of claim 1 having the structure:

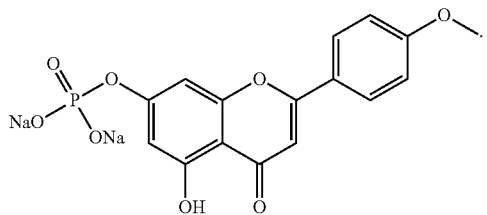

6. The compound of claim 1 having the structure:

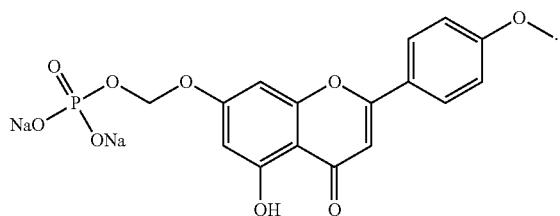

7. The compound of claim 1 having the structure:

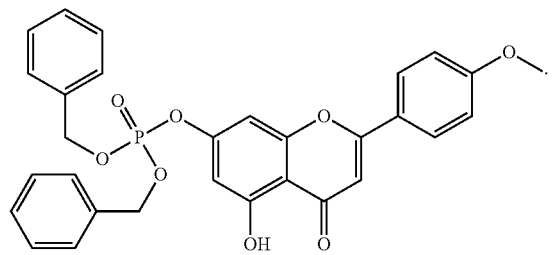

8. The compound of claim 1 having the structure:

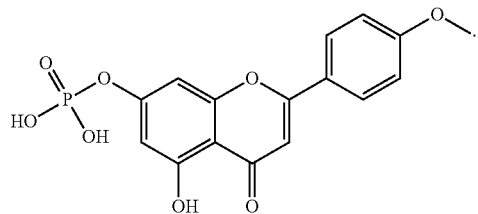

9. A pharmaceutical composition comprising the compound of claim 1 and one or more pharmaceutically acceptable carriers.

10. A pharmaceutical composition comprising the compound of claim 2 and one or more pharmaceutically acceptable carriers.

11. A pharmaceutical composition comprising the compound of claim 3 and one or more pharmaceutically acceptable carriers.

12. The composition of claim 9, wherein the compound is selected from the group consisting of:

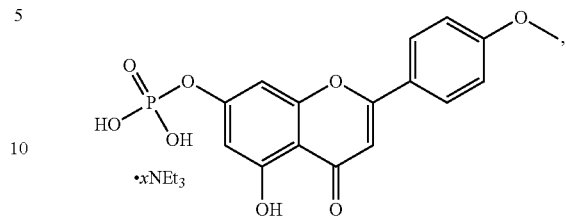

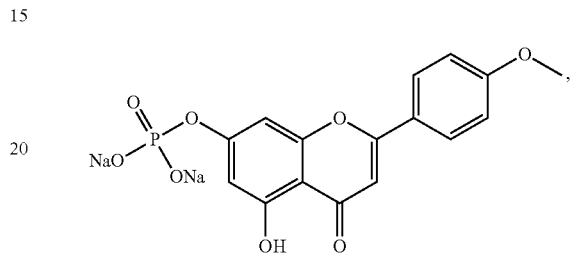

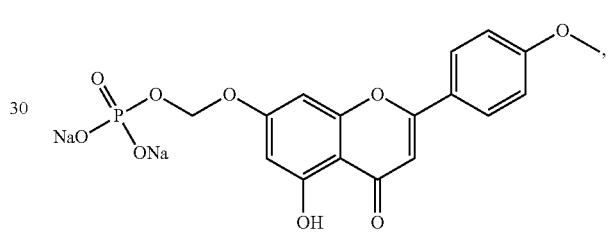

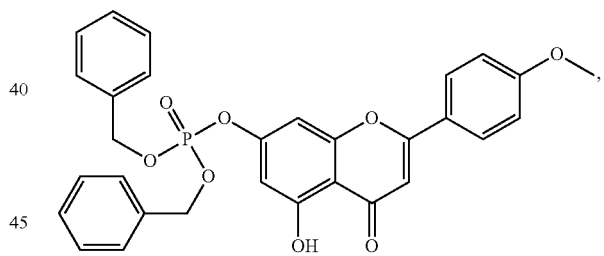

and

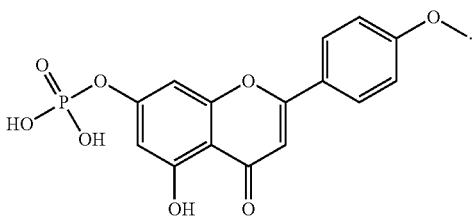

13. A method for treating myocardial infarction, comprising administrating to a patient in need thereof an effective amount of a water soluble compound of Formula I of claim 1, alone or in combination with acacetin.

14. The method of claim 13, wherein the compound is a compound of Formula IIA of claim 2.

15. The method of claim 13, wherein the compound is a compound of Formula IIB of claim 3.

16. The method of claim 13, wherein the compound has the following structure:

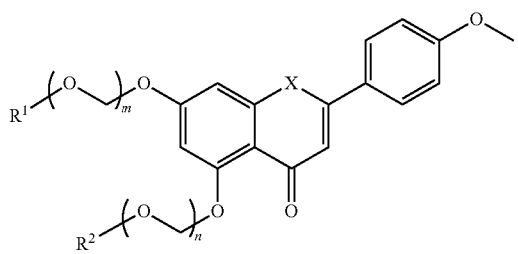

| Compound | X | m | R¹ | n | R² |
|---|---|---|---|---|---|
| A | O | 0 | P(O)(OH)₂•x(NEt₃) | 0 | H |
| B | O | 0 | P(O)(ONa)₂ | 0 | H |
| C | O | 1 | P(O)(ONa)₂ | 0 | H. |

17. The method of claim 13, wherein the effective amount is from about 0.001 to about 100 mg/kg of the body weight of the patient per day.

18. The method of claim 13, wherein the patient is a human.

19. A method for treating ventricular arrhythmia, comprising administrating to a patient in need thereof an effective amount of a water soluble compound of Formula I of claim 1, alone or in combination with acacetin.

20. A method for inhibiting ventricular arrhythmia, comprising administrating to a patient in need thereof an effective amount of a water soluble compound of Formula I of claim 1, alone or in combination with acacetin.

* * * * *